United States Patent [19]

Barber et al.

[11] Patent Number: 4,858,121
[45] Date of Patent: Aug. 15, 1989

[54] MEDICAL PAYMENT SYSTEM

[75] Inventors: William B. Barber, Berea; William H. Davis, Fairview Park, both of Ohio; Karl Rautenkranz, Tucson, Ariz.

[73] Assignee: Medical Payment Systems, Incorporated, Westlake, Ohio

[21] Appl. No.: 940,559

[22] Filed: Dec. 12, 1986

[51] Int. Cl.$^4$ .................... G06F 15/42; G06F 15/30
[52] U.S. Cl. ................... 364/406; 364/413.01; 235/380
[58] Field of Search ............ 364/406, 413; 235/380

[56] References Cited

U.S. PATENT DOCUMENTS

| 4,319,225 | 3/1982 | Klose | 340/347 DD |
| 4,454,414 | 6/1984 | Benton | 364/406 X |
| 4,632,428 | 12/1986 | Brown | 283/112 X |
| 4,648,037 | 3/1987 | Valentino | 364/408 |
| 4,667,292 | 5/1987 | Mohlenbrock | 364/406 |

Primary Examiner—Jerry Smith
Assistant Examiner—Steven Kibby
Attorney, Agent, or Firm—Fay, Sharpe, Beall, Fagan, Minnich & McKee

[57] ABSTRACT

A plurality of remote terminals (A) are each disposed in a physician's office and are connected by telephone lines or other electronic data communication with a central processing system (B). Each terminal includes a data entry key board (10) and a magnetic tape reader (12) for entering physician, patient, medical service, insurance, and other medically related data. The entered data is processed by a terminal processor (20) to incorporate previously stored data from an electronic data memory and to transfer and store entered medical transaction data to memory. The central processing system includes a physician file for storing participating physician identifications for verifying received physician information data, a patient memory for storing participating patient data for verifying received patient identification data, an insurance company file for storing appropriate format for medical claims for each of a plurality of participating insurance companies, and a claims file for storing a record of medical insurance claims processed. A central processing computer processes the received data and formats it into the appropriate format for a medical claim to the identified insurance company. A printer (D) or an electronic data transfer (C) transfers the medical claims from the central processing system directly to the insurance companies. Electronic funds transfer facilities at the central processing station and at one or more banks or financial institutions are called upon to transfer funds directly to a physician's account and to acknowledge receipt of funds from insurance company accounts.

17 Claims, 23 Drawing Sheets

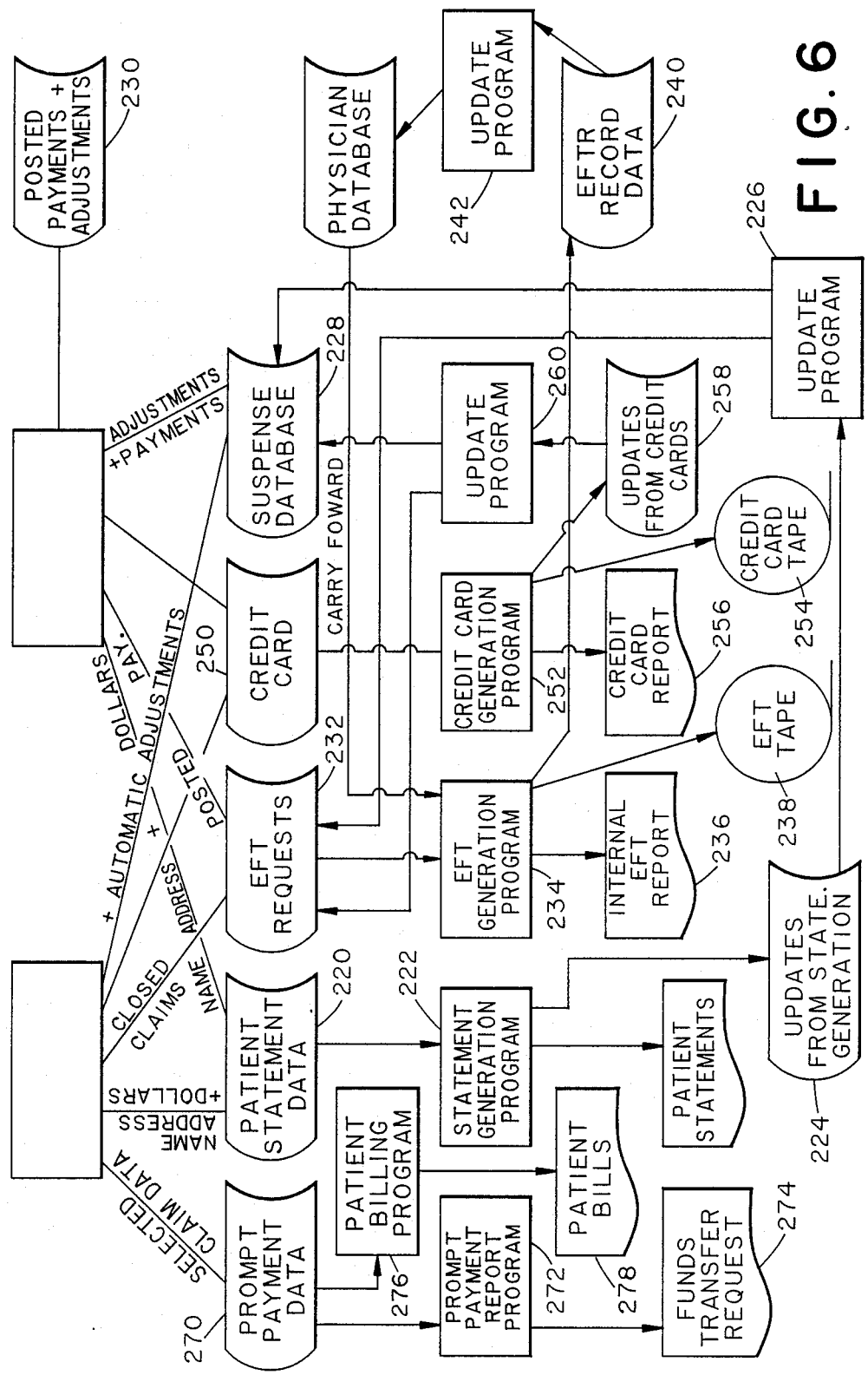

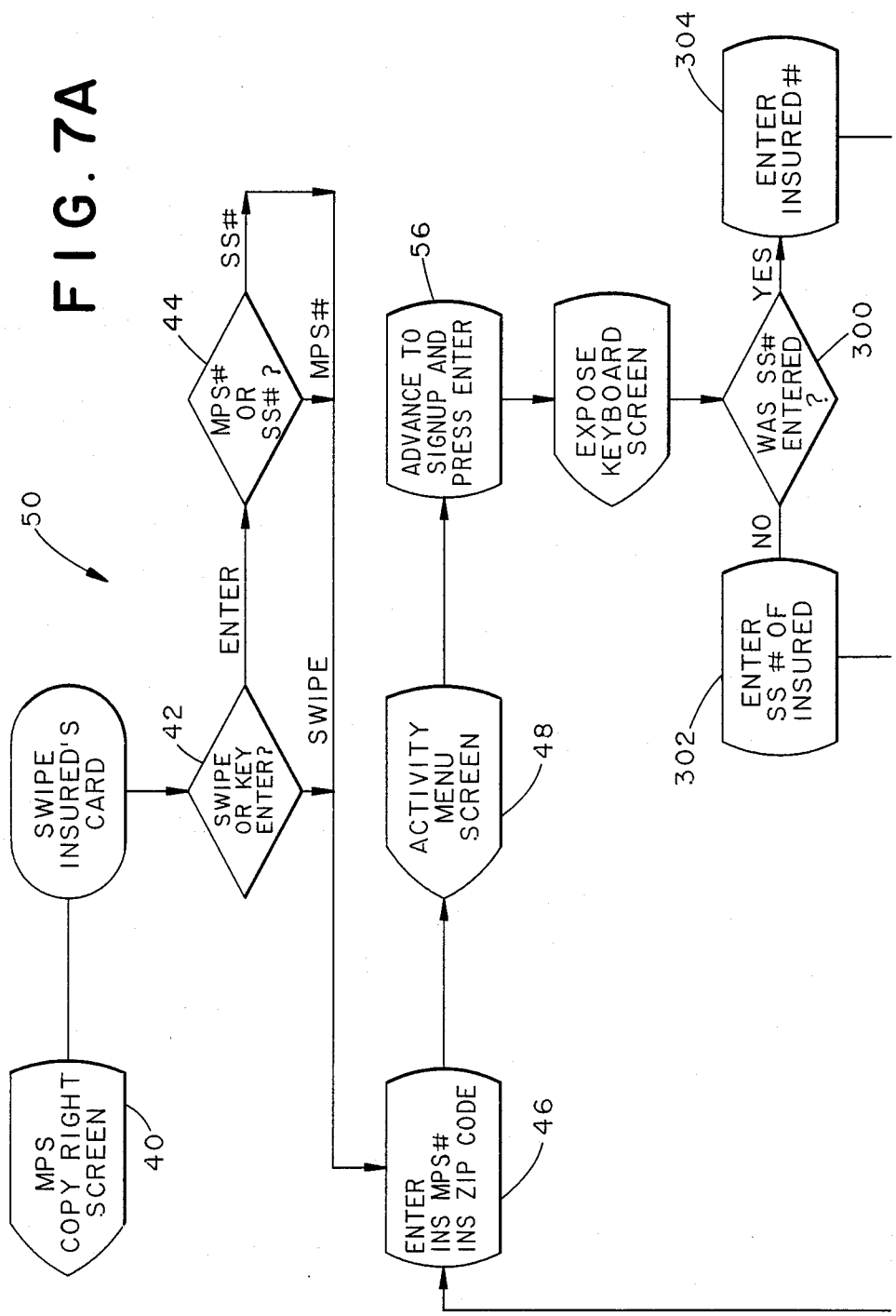

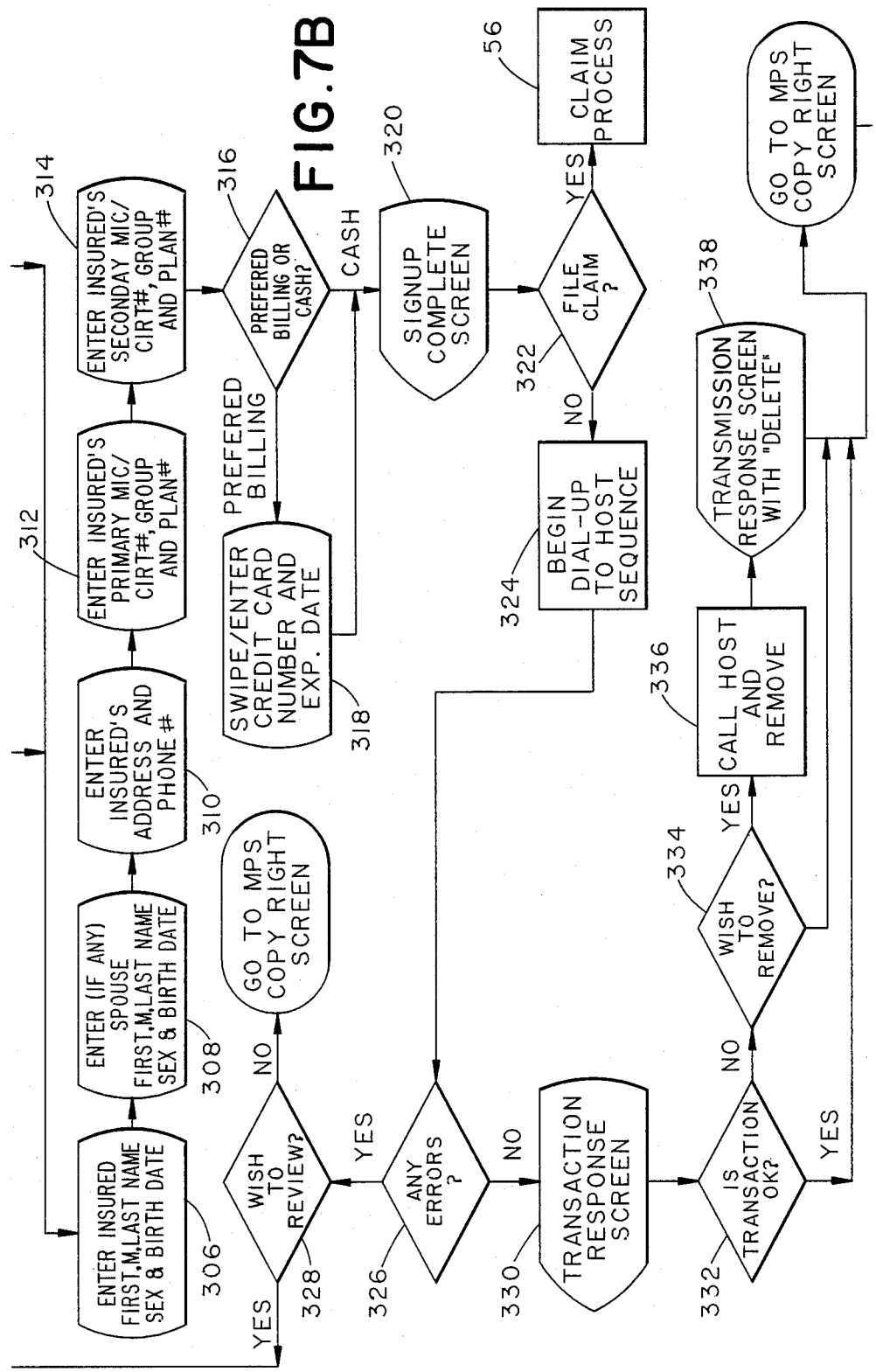

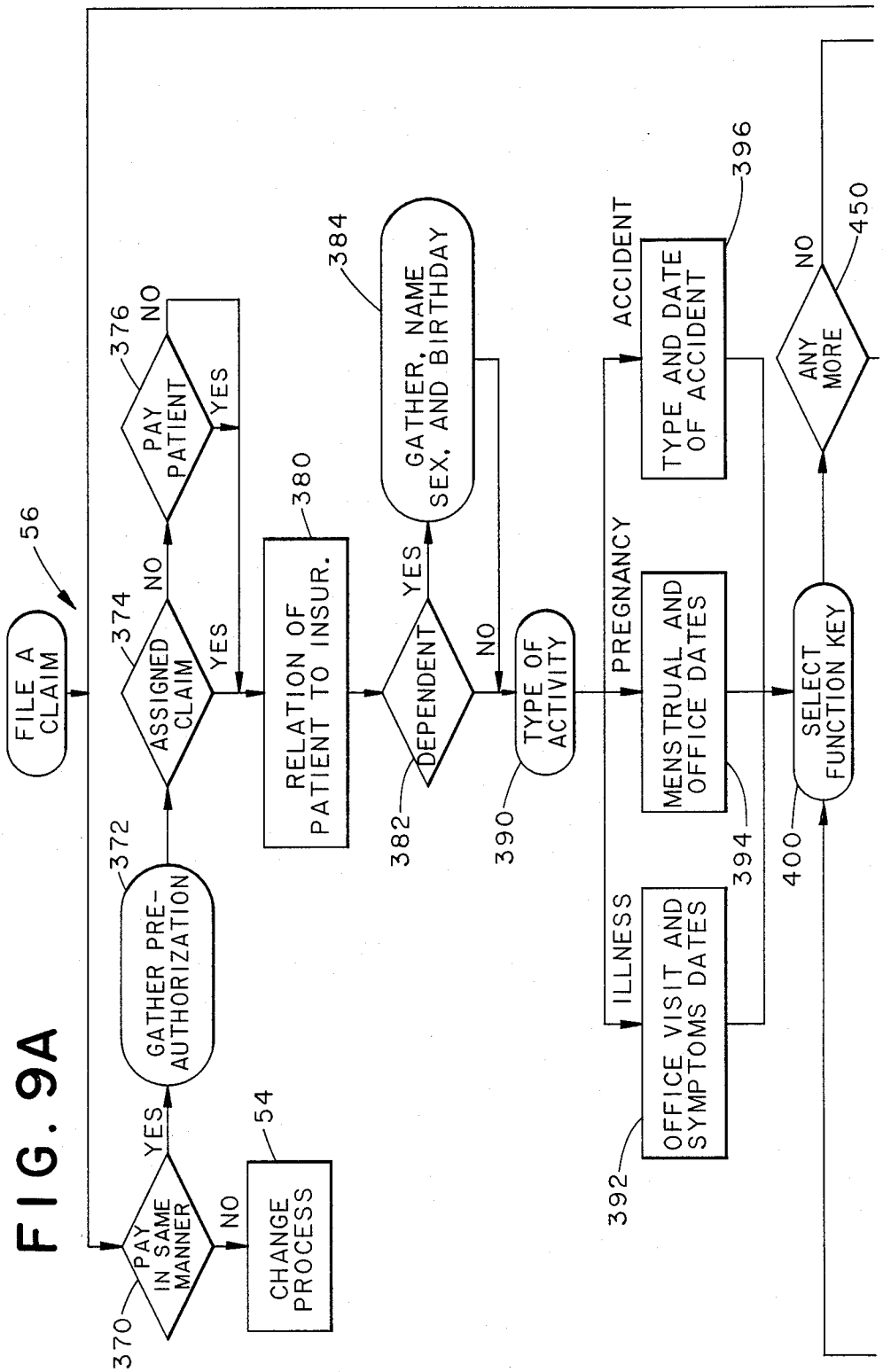

FIG_14

MEDICAL PAYMENT SYSTEM

BACKGROUND OF THE INVENTION

The present invention relates to the computerized financial transactions art. It finds particular application in conjunction with reimbursements made for physician's services and the processing of medical insurance claims.

Heretofore, it has been necessary for physicians to process a wide variety of papers and forms to receive compensation for their services. The numerous insurance companies which have provided medical insurance to the consuming public have had a wide range of different forms which must be submitted to receive compensation. Some of the forms were to be submitted by the doctors and others were to be submitted by the patients. Under some insurance policies, the patient has been a co-insurer who was responsible for a portion of the medical bills. In other instances, the physican's fees have exceeded the compensation paid by the insurance company, leaving a balance to be paid by the patient. Some insurance companies have paid the benefits directly to the patient and the patient has reimbursed the doctor; whereas, other insurers have paid the doctor directly. Even as to monies paid by the patient, some patients paid by check or cash at the time the services were rendered, some paid by credit card, and others were invoiced. The processing of the numerous different types of insurance forms and modes of payment has created a major paper processing problem. Many physicians and clinics have had to hire extra staff whose sole job function was to handle this paperwork. The extra staff increased over head which was passed on to the consumer in the form of higher medical bills.

Even once the forms were filled out and submitted, the physician still faced the problem of collecting the amounts invoiced to the insurance companies and patients. Forms which were filled out improperly were commonly returned to the physcan to be processed again. Even forms that were properly filled out commonly required extended durations for processing by the insurance companies before reimbursement checks were mailed. In some instances, the processing time was several months. If the claim exceeded the limits of the insured policies, the same processing time elapsed before the physician was advised that he was receiving only partial payment. Partial payments by the insurance companies necessitated invoicing the patients, possibly months after the services were provided. These delays between the time the services were provided and when compensation was received again increased the physician's overhead. This increase in overhead again resulted in higher medical costs to the consumer.

The present invention provides a new and improved computerized financial transaction system for physcians and other medical personnel which overcomes the above referenced problems and others.

SUMMARY OF THE INVENTION

In accordance with one aspect of the present invention, a financial transaction system is provided for physicians' offices. A plurality of physician terminals, which are located in physicians' offices, are interconnected with a central processing system. Each physician terminal includes means for entering at least a patient identification, a medical service identification, a physician identification, and an insurance carrier identification. Each terminal further includes a modem means for electronically conveying the entered identifications to a modem means of the central processing system. The central processing system includes a patient file means for verifying the patient identification and a physician file means for verifying the physician identification. A claims means transforms the received identifications into a preselected format for the identified insurance company.

In accordance with a more limited aspect of the invention, each physician terminal includes a key board array for entering identifications, a swipe card reader for reading identifications electronically from a card, and a display terminal.

In accordance with another more limited aspect of the present invention, the central processing system includes a statement means for providing periodic statements of charges and payments for one or more of the physicians, the patients, and the insurance companies.

In accordance with another more limited aspect of the present invention, the central processing means includes a funds transferring means for transferring funds collected from the insurance carrier directly to a bank account of the appropriate physician.

In accordance with yet another more limited aspect of the present invention, a data link is provided between the central processing system and computers of one or more of the insurance companies for electronically conveying claims from the claim means directly into the insurance companies' computers.

A primary advantage of the present invention is that it expedites the processing of medical claims and bills.

Another advantage of the present invention is that it reduces the cost of claims processing and speeds the collection of fees by physicians.

Another advantage of the present invention is that it reduces the cost of claims processing by insurance companies.

Yet another advantage of the present invention is that it standardizes the insurance claims and medical payment procedure for patients and reduces medical costs through reduced overhead.

Still further advantages of the present invention will become apparent to those of ordinary skill in the art upon reading and understanding the following detailed description.

BRIEF DESCRIPTION OF THE DRAWINGS

The present invention may take form in various components and arrangements of components and in various steps and arrangements of steps. The drawings are only for purposes of illustrating a preferred embodiment and are not to be construed as limiting the invention.

FIG. 6 is an overview process flow for data handling after entry;

FIG. 7 is a detailed illustration of the data processing at the physician terminal for a sign-up process;

DETAILED DESCRIPTION OF THE PREFERRED EMBODIMENTS

Figure 1:
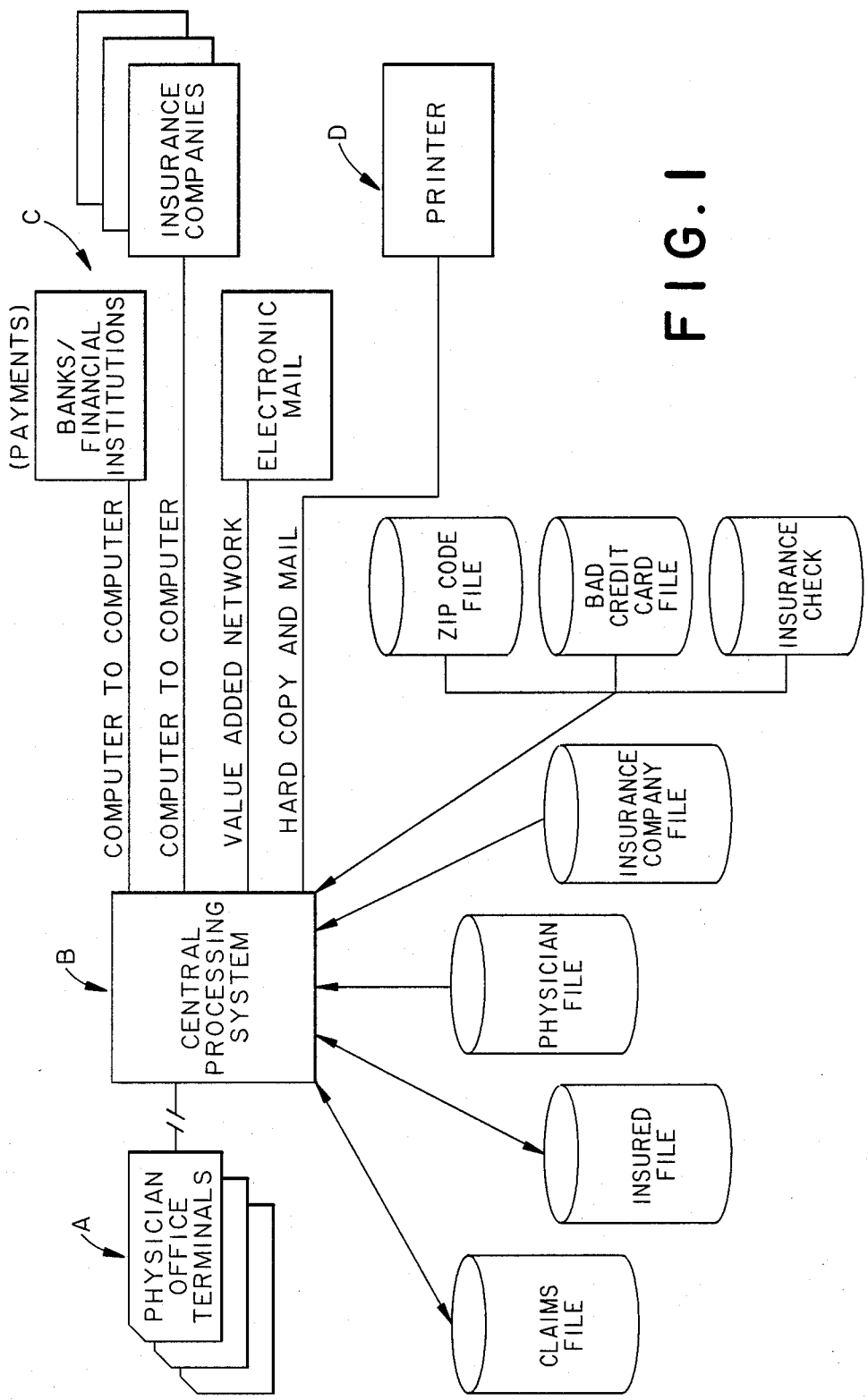
FIG. 1 is an overview of a financial transaction system in accordance with the present invention.

With reference to FIG. 1, the medical payment system includes a plurality of remote terminals A that are interconnected with a central processing system B. Each remote terminal is disposed in a physician's office or other medical facility and is interconnected with the central processing system by existing telephone lines or other data links. The central processing system is interconnected with other electronic and computerized equipment C, commonly at remote locations. In particular, the central processing system may be interconnected directly with insurance companies, banks and financial institutions, electronic mail facilities, and the like to communicate information electronically therebetween. Data which cannot be communicated electronically is conveyed to a printer D to print a hard copy.

At each remote terminal, data are entered regarding charges and payments for medical services. The information which is forwarded from the remote terminals to the central processing system includes identifications of the physician, the patient, the medical service, and the patient's insurance carrier. Additional information may also be transmitted, such as a credit card identification for credit card payments, check and bank information for check payments, cash payments, no charge services, or the like. The central processing system verifies the physician, patient, and insurance company identifications. The services, physician, and patient identifications are reformatted into the appropriate format for claims of the identified insurance carrier. Preferably, the claims data are electronically communicated directly to the computers of the insurance companies. Where appropriate, printed claims are prepared on the printer D and forwarded to the insurance carrier.

The insurance carrier returns financial credit information, preferably by an electronic funds transfer. When funds are received from the insurance company, whether by check or electronic funds transfer, the central processing system B communicates directly or by printed authorization with the computers of banks and other financial institutions to transfer the appropriate funds to the account of each physician. For patients whose insurance contract only provides less than full compensation for the services provided, the central processing system B determines the balance due from the patient and notifies the remote terminal. The balance may be paid by credit card through the central processing system, cash, or by a billing generated by the central processing system. The funds are again transferred through or at least recorded by the central processing system such that statements can be provided on a monthly or other regular basis to the physician and, where appropriate, to the patient.

Figure 2:
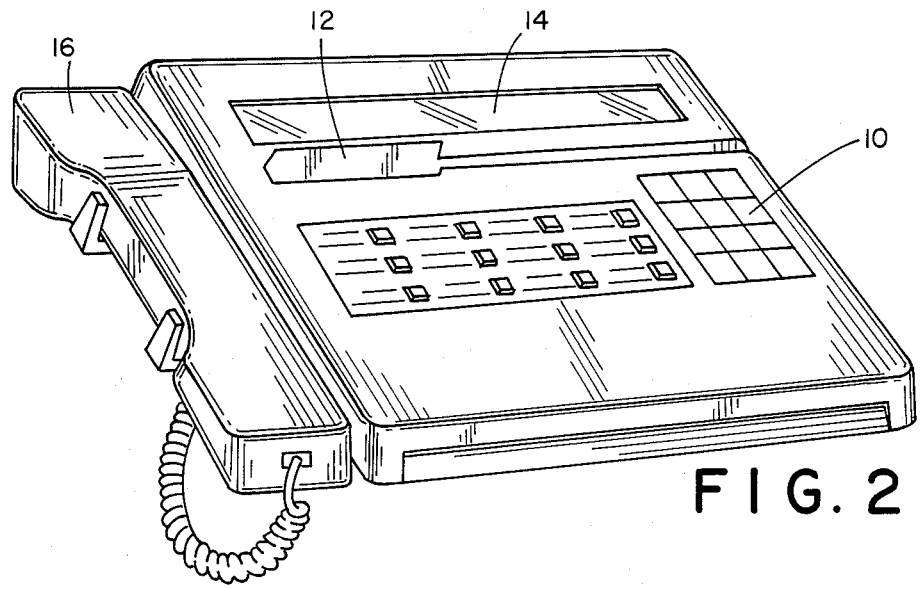
FIG. 2 illustrates a physician's office terminal.

With reference to FIG. 2, each remote terminal includes a manual data entry keyboard 10 for entering medical service and other data. A card reader 12 reads patient identification cards, physician identification cards, credit cards, and the like. Preferably, the card reader includes a swipe reader that reads magnetic tape affixed to the cards. However, the reader may be configured to access the processor of smart cards, to read bar codes, to read infrared codes, or the like as may be appropriate to the format. Commonly, the patient identification and the insurance company identification are read from the patient's identification card and the physician's identification is read from a physician identification card and stored in the terminal. However, on initially signing up or when changing patient records, patient information is entered on the keyboard. A display or area means 14 presents entered data, messages concerning entered data, and responses from the central processing system. A voice communication means or telephone receiver 16 enables an operator to communicate by voice with operators at the central processing station and otherwise functions as a conventional telephone receiver.

Figure 3:
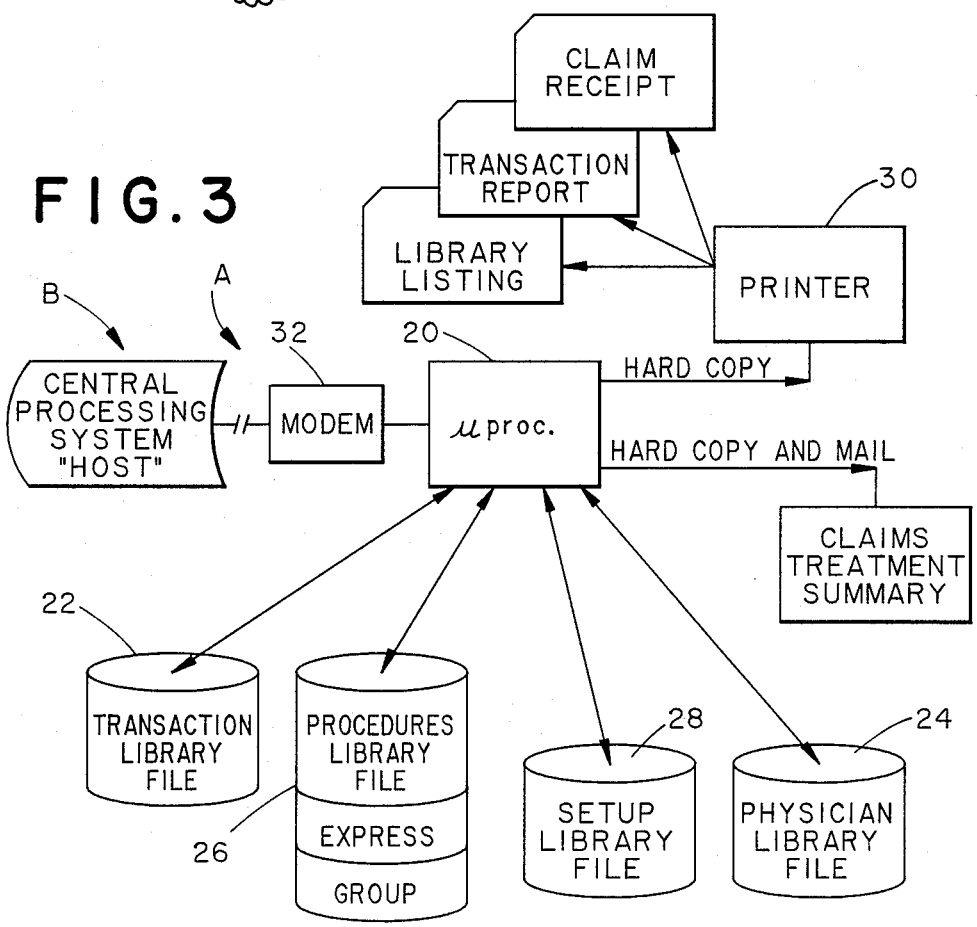
FIG. 3 is an overview of a process flow for the physician's office terminal.

With reference to FIG. 3, each remote terminal has a computer 20 which is preprogrammed to carry out preselected routines. The computer includes a transaction memory or library file 22 for storing each entered medical claim to provide an on-site record. A physician library file 24 stores physician information for each physician in the practice, who is frequently consulted, or whose services are otehwise billed through the remote terminal. A procedures library or memory means 26 stores the medical services or procedures most routinely performed by the physicians. When entering a claim, the common details of these procedures are retrieved from memory rather than being reentered every time. A set-up library file or memory means 28 enables additional storage files to be set-up as may be required by the physician, e.g. a daily report generator. A printer 30 may be provided for printing patient receipts, daily physician statements or reports, insurance company claims for submission by a patient for reimbursement, or the like. A modem 32 communicates with the central processing system B over telephone or other data communications lines.

Figure 4:
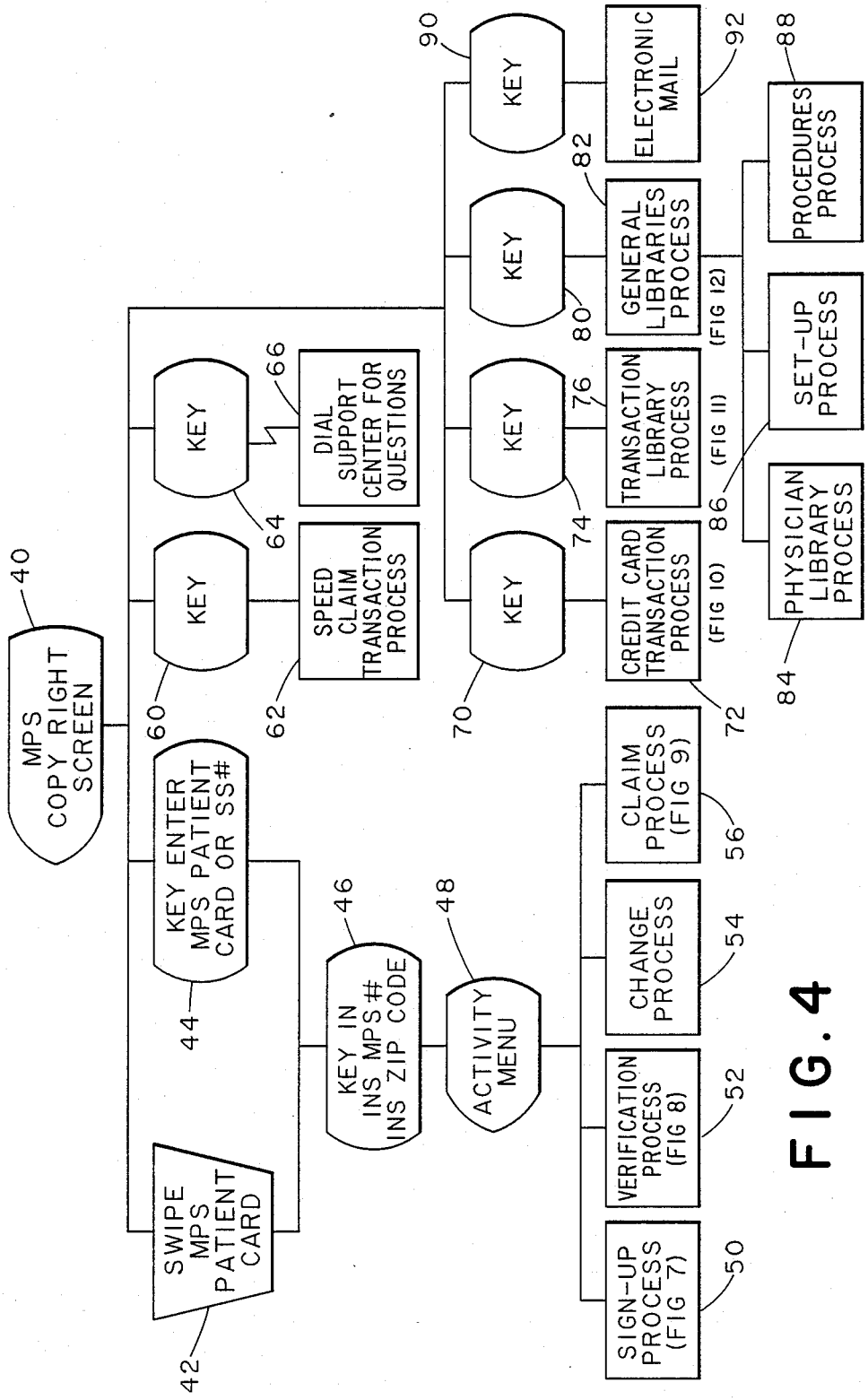
FIG. 4 is a more detailed process flow for the office terminal.

With reference to FIG. 4, the display means 14 displays an indication 40 that the computer 20 is ready for use in a ready state. The computer receives the patient's identification number by accessing the swipe card reader at 42 or by monitoring the keyboard at 44. Additional identifications 46 are keyed in as a cross check on the authenticity of the patient card. Such cross check information may include the patient's zip code, family history, social security number, or the like. A display control 48 displays selectable routines that may be chosen including a sign-up process 50, a claims process 56, a verification process 52, a change process 54, which are described in greater detail in conjunction with FIGS. 7–10, respectively, below.

The remote terminal also permits the operator to select specialized functions. For example, at 60 the operator can command the terminal to bring up a speed claim procedure 62. In the speed claim procedure, a library or memory within the remote terminal, which has a plurality of prestored medical service information therein, is accessed. Commonly, as described below, the physician has entered the information for the two or three dozen most commonly performed procedures in his office. In the speed claim transaction process, the information regarding these most common procedures can be accessed from the procedures library file 26 at the touch of a button and transmitted to the central processing system as part of a claim. This saves re-entering the medical service information in full. At 64 the keyboard also enables the operator to actuate the voice communication means 16 to dial up a question center at 66 to answer data entry questions.

Figure 11A:
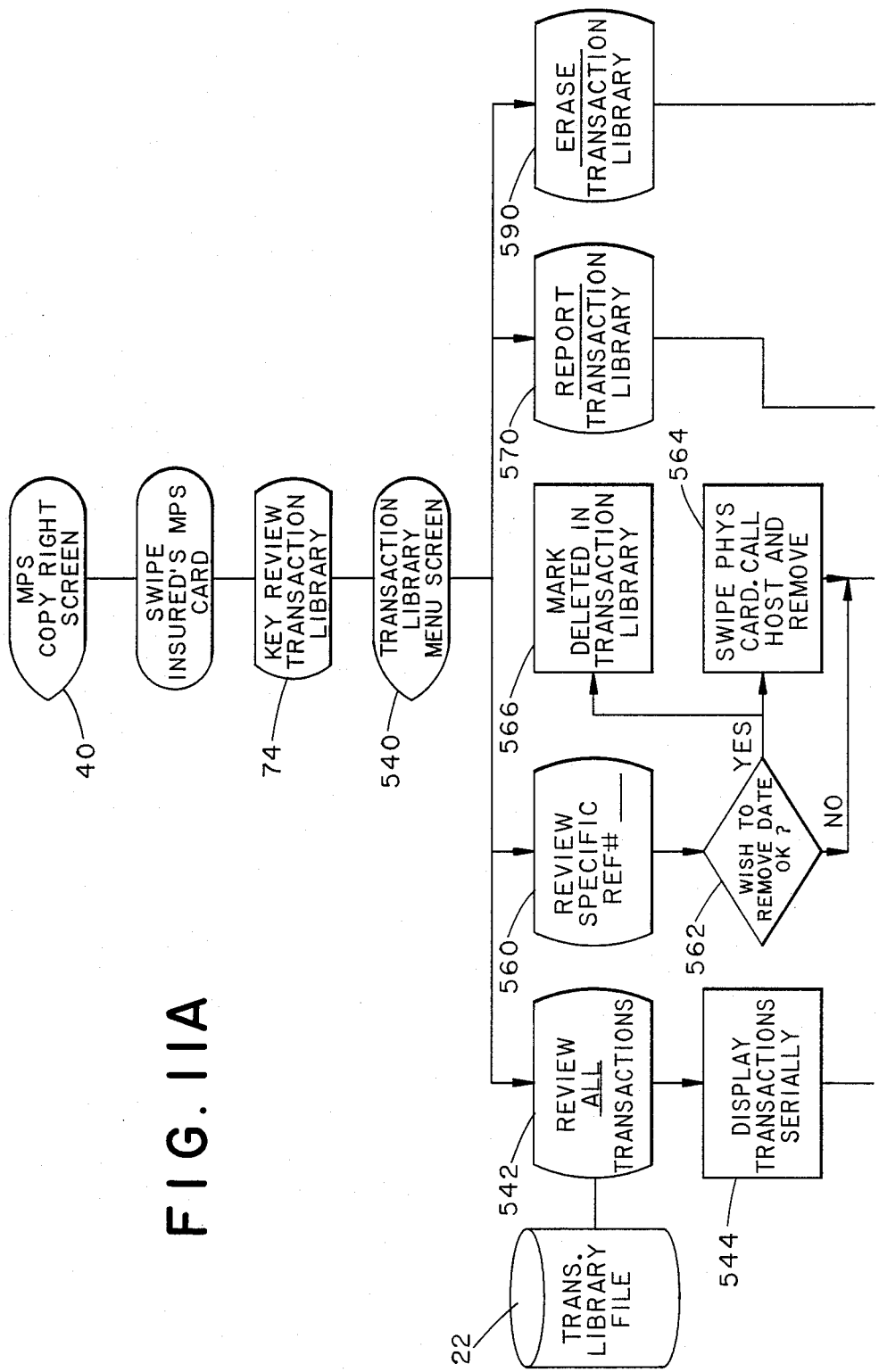
FIG. 11 is a detailed illustration of the transaction data processing procedure at the physician's terminal.
Figure 11B:
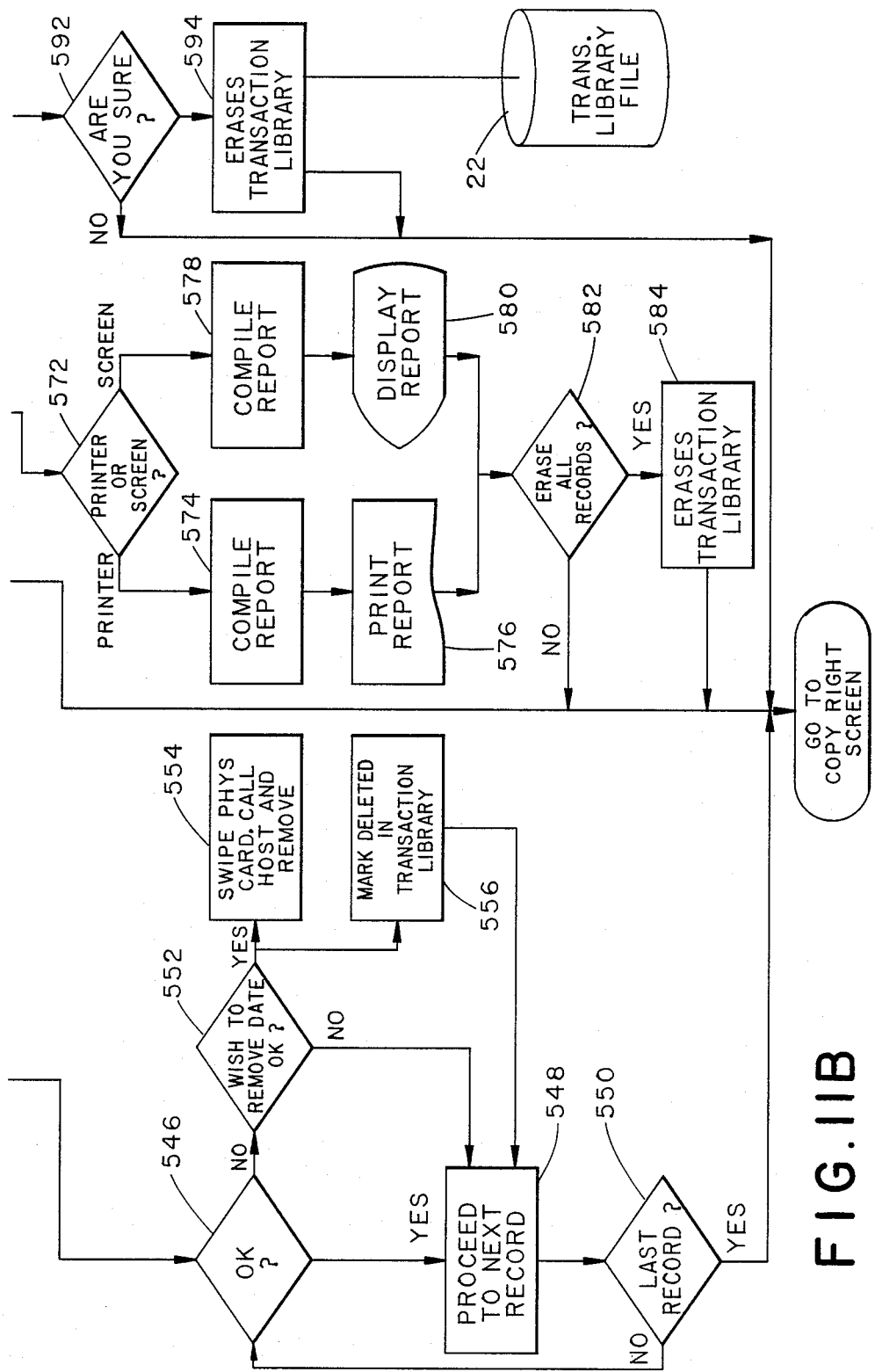

The operator may also key at 70 a command to bring up a prerecorded credit card transaction procedure 72 described in greater detail in conjunction with FIG. 11. The credit card transaction procedure brings up on the display screen 14 a series of questions and instructions to walk the operator through a credit card transaction. The credit card transaction process further formats the requested credit card information appropriately for transmission to the central processing system. A transaction library key 74 enables the operator to initiate a transaction library process 56. The transaction library enables the operator to review each medical service payment transaction entered through the remote terminal. The operator may also correct or edit transaction data. Reports and compilations of the stored data are also retrievable.

A library access key 80 enables the operator to enter a general library process 82. The general library process may address a physician library retrieval routine to retrieve background information on physicians from the physician library 24. A set-up process routine 86 allows new and additional libraries to be set up. A procedure process or subroutine 88 enables the physician to prerecord medical service claim information such as fees, place, patient body site, and the like for each of a plurality of regularly performed covered physicians' treatments. This enables the speed claims of process 62 to be customized to the physician's practice. The fees may be set in accordance with groups, insurance companies, or the like. When the patient identification, insurance company, and medical treatment are entered as part of a claim, the appropriate supporting information about the treatment including the fee are retrieved from the procedure library 26 and need not be reentered for each claim.

An electronic mail key 90 enables an electronic mail procedure 92 to be entered. The electronic mail procedure provides for the same or next day delivery of insurance claims, patient statements, and the like.

Figure 5A:
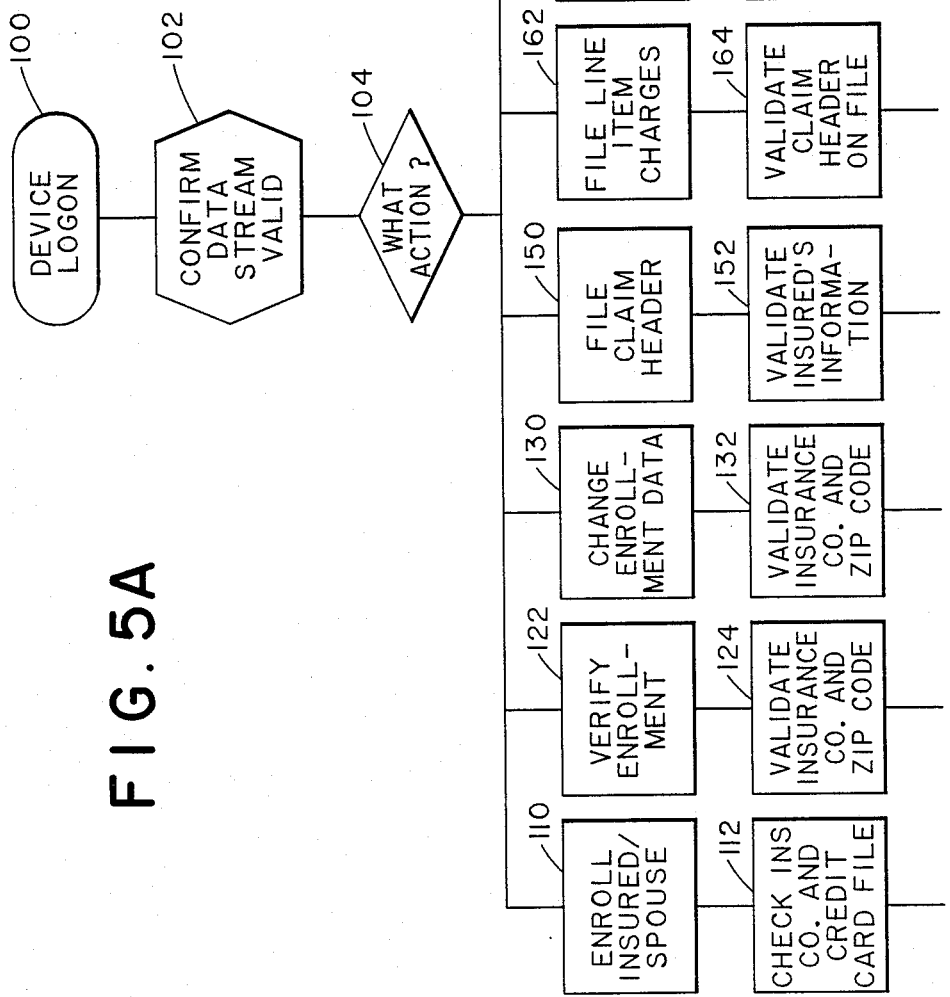
FIG. 5 is a diagrammatic overview of the central processing system.
Figure 5B:
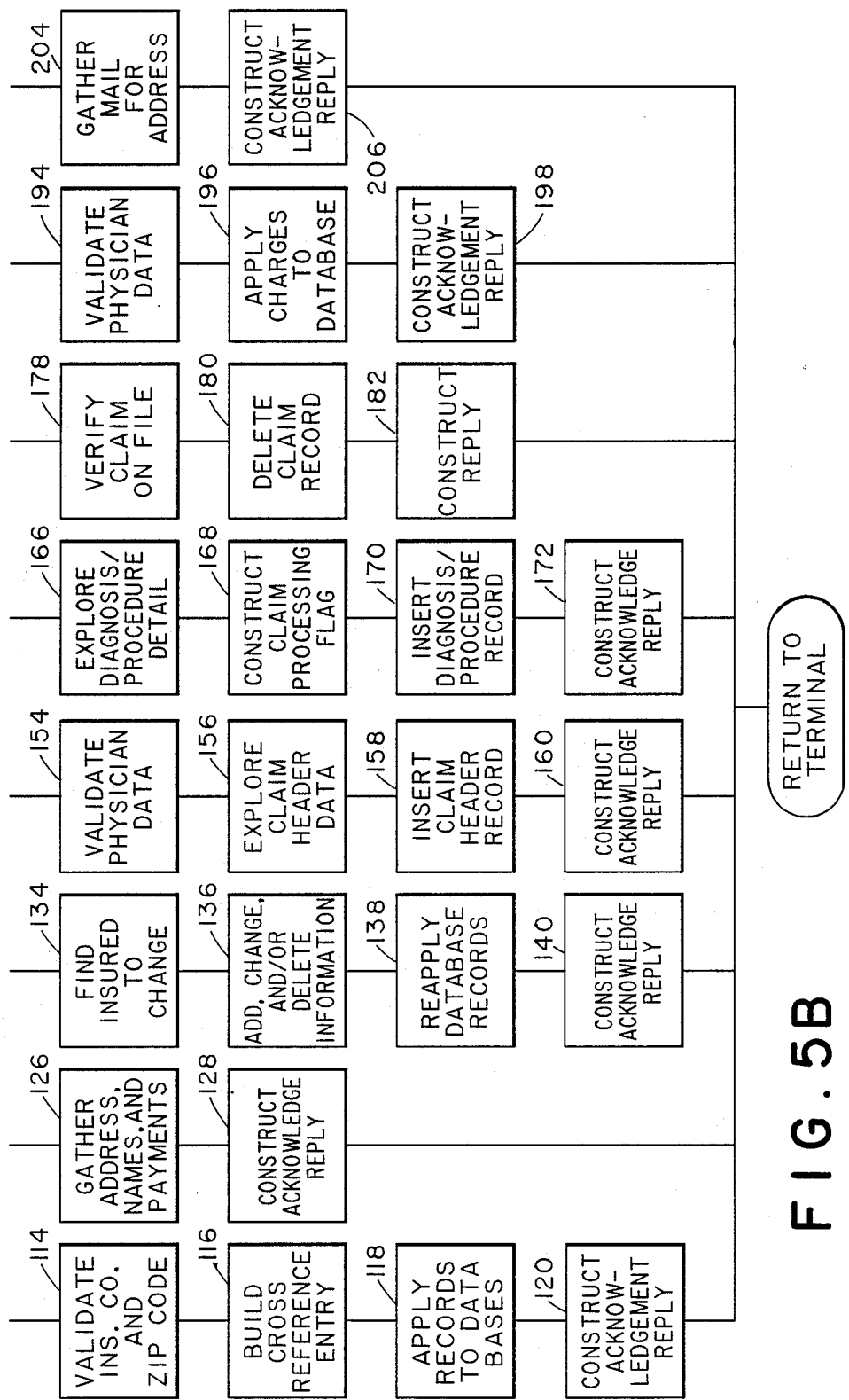

With reference to FIG. 5, the interaction of the central processing system B with the remote terminal is described in greater detail. First, each terminal logs on at 100 and a confirmation of a valid data stream is made at 102. An indication of the action to be taken is selected at 104.

If the sign-up procedure 50 is selected, an enrollment routine 110 is initiated. Entered insurance company information and credit card information is cross checked with data on store at the central processing system at 112. The entered insurance company and zip code are validated at 114. Selected portions of the data are identified at 116 and used to build cross reference indices. At 118, the new patient data including the patient identification, insurance company, and zip code are entered into the appropriate data bases. An acknowledgement is constructed at 120 and returned to the remote terminal for display.

If the verification process 52 has been selected, an enrollment verification routine 122 is initiated. The insurance carrier and correspondence between the entered and prerecorded patient's zip code is validated at 124 to assure that the change is authorized. Records of the patient's name, address, and patient history are retrieved at 126 from memory and revised. An acknowledgement reply is constructed at 128 for return to the remote terminal for display to the operator.

If the enrollment change process 54 has been selected, a change enrollment data procedure 130 is initiated. The insurance company identification and zip code are validated at 132. The insured's record is located within the insured or patient file at 134 and the appropriate changes and deletions to the patient information are made at 136. The revised records are reapplied at 138 to the appropriate data bases. An appropriate acknowledgement is constructed at 140 for return and display on the remote terminal.

If the claim process 56 has been selected, a claim header, i.e. basic claim information including patient, physician, medical service fee, insurance company and other identifications, are filed at 150. Information about the patient or insured is validated at 152. For example, the patient identification, zip code, or the like may be compared with data stored in a patient or insured file at the central processor to assure that the transaction is charged to the proper insured. Next, at 154 the physician identification is validated. Again, the received physician identification may be compared with data in a prerecorded physician's file. For compactness of data transmission, the claim information may be transmitted in a relatively compact form which is then expanded at 156. An appropriate claim record is formated at 158 and stored for dialog transmission to the appropriate insurance carrier. At 160 an acknowledgement reply is generated to the remote terminal to provide an indication on the display means 14 that the transaction is complete or, if appropriate, that there was an error in the received data.

If the physician charges are to be amended, a line item charge file process is initiated at 162. The claim header is validated at 164 and the diagnosis or procedure described in the claim header is exploded at 166 by retrieving information on the identified procedure from memory. A claim processing flag is generated at 168. The diagnosis, procedure, and fees are entered at 170 into the patient, insurance, and other appropriate data bases. An appropriate acknowledgement is constructed at 172 and returned to the remote terminal for display.

If a previously filed claim is to be deleted, a claim purge process 174 is initiated. The physician identification data is validated at 176 to be sure the treating or other authorized physician is changing the claim. The program determines at 178 whether the claim in question was previously filed and stored in the central processing computer memory. The claim in question is deleted from the file at 180. A reply is constructed at 182 acknowledging the purge and returned to the remote terminal for display on the display means 14. The acknowledgement indicates either that the claim has been deleted or that there is an error in the instructions and that it has been completed.

If a credit card transaction was selected at 72, then a credit card charge routine 190 is entered. The credit card number is validated at 192 by comparison against an invalid credit card list. The physician identification is validated at 194. The appropriate charges are applied to the credit card data base and credited to the physician's account at 196. An acknowledgement is constructed at 198 and returned to the remote terminal.

If an electronic mail procedure was selected at 92, an electronic mail processing routine 200 is entered. The electronic address is validated 202. At 204, all electronic mail going to the same address is gathered so that all mail is sent at regular intervals. An acknowledgement is constructed at 206 and returned to the remote terminal.

With reference to FIG. 6, various financial transactions and reports are generated by the central processing system as a result of the entered claim and other information.

The central processing system separates patient statement data at 220 and generates patient statements 222. Updates from generating the patient statement are monitored at 224 and entered at 226 in the patient, physician, insurance company, and other appropriate data bases. Patient payments or failure to pay are recorded in an accounting file 228.

When funds have been received from the insurance company at 230, any compensated prompt payment claims are closed. The electronics transfer routine is requested at 232. An electronic funds transfer generation program 234 generates a printed report 236 and an electronic funds transfer tape 238 for transmission to a bank or other financial institution which credits the funds to the physician's account. Electronics funds transfer data is recorded at 240. An up-date program 242 updates the data stored in a physician payment file 244 to reflect the electronic funds transfer payment data.

A credit card program 250 enables a credit card generator program 252 to create a credit card tape 254 for transmission to the appropriate credit card company and enables a printed report 256 to be made up for bookkeeping purposes. A credit card up-date program 258 monitors the information from the credit card transaction. An up-date program 260 causes the up-date from the credit card transactions to be stored in the accounting data base 228.

Claims are designated by the physician to be early or prompt payment claims or segregated into a prompt payment fund 270. After a preselected number of days, e.g. fourteen, the amounts covered by insurance on the prompt payment claims are organized by physician and a report generating step 272 to create a funds transfer request 274. The electronic funds transfer request may be an electronic funds transfer or may be a funds transfer authorization transferred to a selected financial institution. For a prompt payment patient claim for which payment has been refused or reduced by the insurance company, a patient billing routine 276 generates patient bills 278 for the difference or deficit.

In this manner, claims information is received at a central processing system from a plurality of remote terminals. The central processing system sorts the claims by insurance company and reformats the claims into the appropriate format for each insurance company. Where appropriate, patient bills and credit card fund transfers are also made. As funds are returned from credit card companies, insurance companies, or patients, the funds are credited to the physicians' accounts. The financial record of claims made, claims outstanding, funds received, any loans against accounts receivable, and the like are collected and printed as a physician's financial statement. The funds that have been credited to the physicians' accounts are transferred electronically or by paper to the physician's account at an appropriate financial institution.

The details of the data handling of the remote terminals A are set forth in FIGS. 7-12.

With reference to FIG. 7, the sign-up procedure program 50 first requests at 300 whether the patient's social security number or other portion of the patient identification was entered. If not, the social security is entered at 302. If the patient social security was previously entered, a patient identification number is entered at 304.

Demographic information on the insured patient is entered at 306 such as first, middle, and last names, sex, patient number, and the like. At 308, similar information is entered for the insured's spouse, where appropriate. The insured and the insured spouse address and other joint information are entered at 310. Insurance information is entered at 312 such as the primary carrier, the group, the plan, and the like. Any secondary insurance is entered at 314. To the extent charges are not covered by insurance, an election is entered at 316 to pay by cash or by credit card. If credit card payment is elected, the appropriate credit card information is read from the card's magnetic strip and stored at 318. A display indicating that the sign up is complete is displayed at 320.

At 322, an inquiry is made whether or not a claim is to be filed in conjunction with the sign-up. If a claim is to be filed, the system goes to the claim processing means 56. If no claim is to be filed, a dial up means 324 communicates the sign up information to the host computer at the central processing system B. The host computer determines whether there are any errors in the transmitted data and returns an error or no error indication at 326. If there are errors, the operator may elect at 328 either to review the entered data by returning to step 46 or terminate the sign up procedure. If no errors are present, an acknowledgement is displayed at 330. At 332, the operator verifies that the transaction is proper. If the operator indicates an error in the transaction, then a means 334 allows the operator either to leave the transaction as is, or to have a means 336 delete the sign up data from the host computer. Upon completing the deletion, an acknowledgement 338 is returned to the operator.

Figure 8:
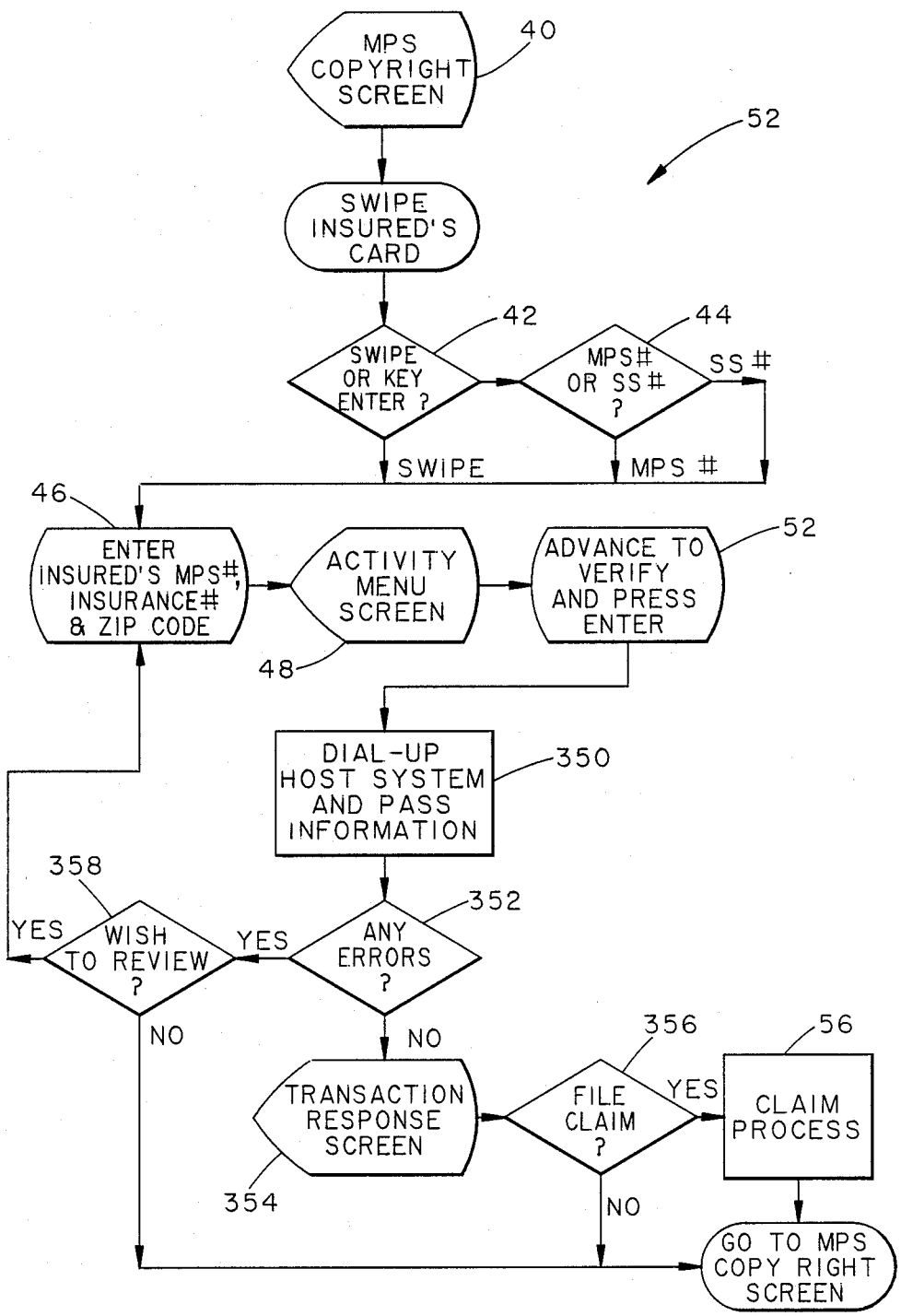
FIG. 8 is a detailed illustration of the verification data flow process at the physician terminal.

With reference to FIG. 8, if the verification process 52 is selected, a dial up means 350 dials up the host computer of the central processing system B and transfers the entered insured patient information. The host computer verifies the information and returns an indication at 352 whether or not there were any errors or discrepancies. If no errors or discrepancies were determined by the host computer, the lack of errors is acknowledged on display means 354. At 356, the operator is given the opportunity to file a medical services claim. If claims are to be filed, the program goes to the claim process 56. If the central computer determines that there are errors, the operator is given the opportunity at 358 to elect whether or not to review the patient information that was sent for verification or return to the ready state 40.

The change process 54 of FIG. 4 is substantially the same as the sign-up process discussed above in conjunction with FIG. 7. The data is called up and reviewed in the same order that it is entered. If any entered data is to be altered or deleted, a prefix indicating an alteration is typed ahead of the substitute data. If a field of entered data is to be erased, an erase prefix or symbol is entered for that field. If neither an alteration nor an erase prefix or symbol is entered, the data remains unchanged.

Figure 9B:
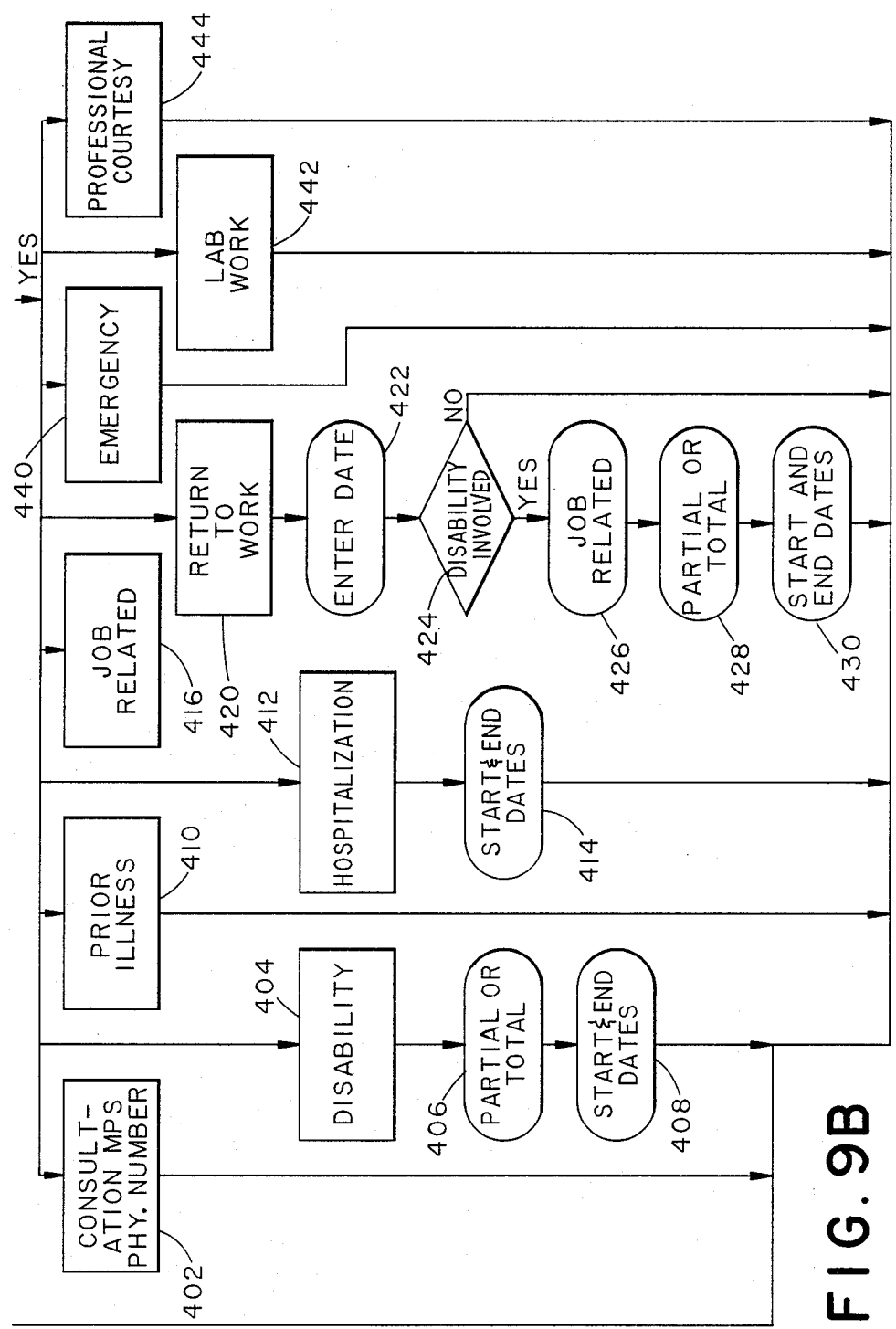
FIG. 9 is a detailed illustration of a claim entry processing at the physician terminal.
Figure 9C:
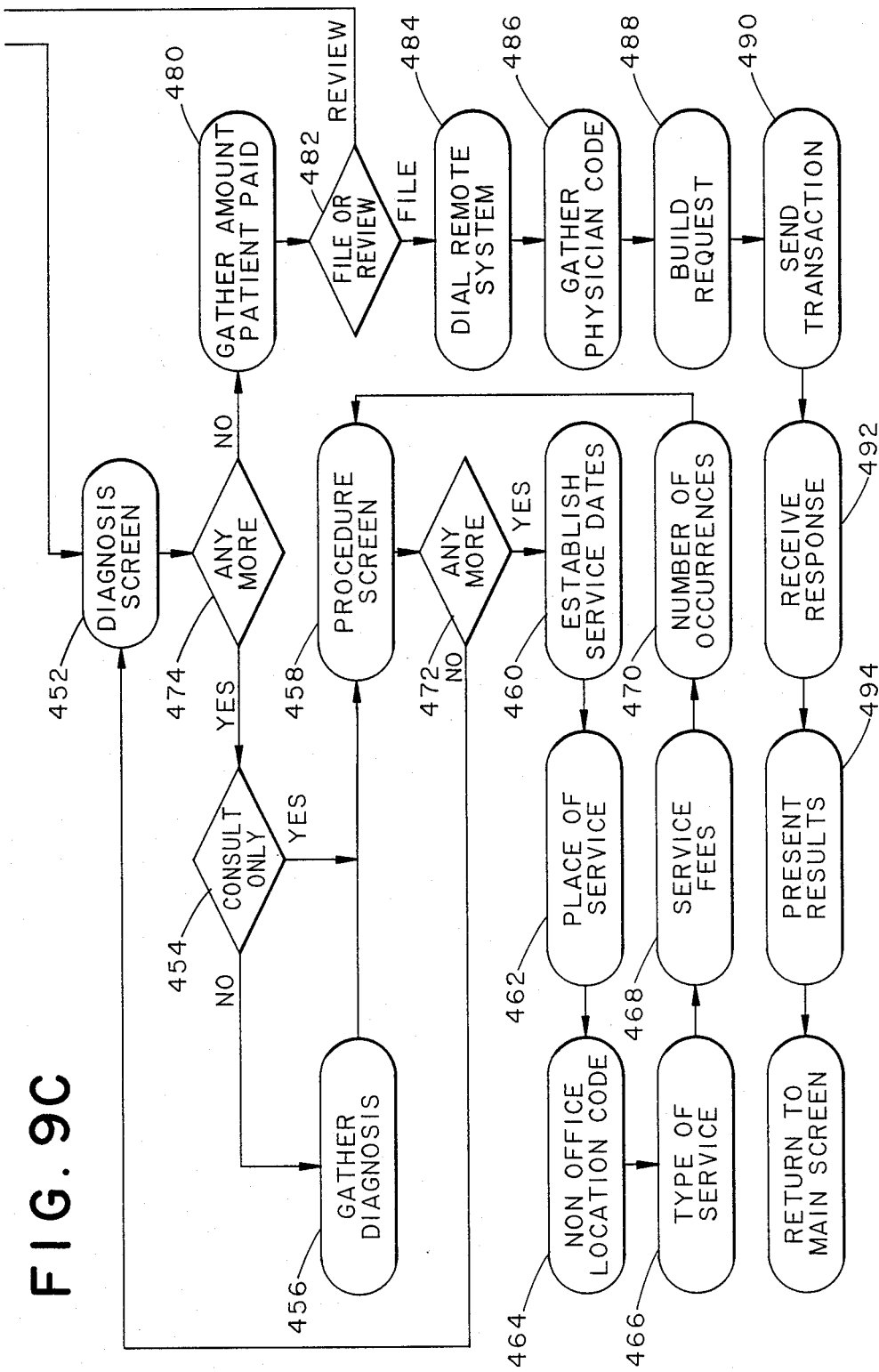

With reference to FIG. 9, when a claim is to be filed, the terminal software checks at 370 whether payment for the service is to be made in the manner previously recorded in the patient's history. If a different mode of payment is selected, the system goes to the data change routine 54 to enter the new payment mode. If the same mode of payment is elected, cross checks are done at 372 on entered and stored patient data to assure that the transaction is authorized by the patient. At 374, the terminal routine determines whether the medical claims are assigned by the patient to the doctor, i.e. whether payment is made from the medical insurance company directly to the doctor or whether the insurance company will pay the patient who will pay the doctor. If the claim is unassigned, then the operator confirms at 376 that payment by the insurance company should go directly to the patient.

Once the payment mode has been determined, the routine determines at 380 whether the patient is the insured or a covered relative of the insured. If it is indicated at 382 that the patient is a covered dependent of the insured, then the patient's name, sex, and birth date are entered at 384.

At 390 the operator enters the type of activity that led to the office visit, e.g. illness, pregnancy, or accident. If an illness is indicated, the dates of office visits and the noted symptoms are entered at 392. If a pregnancy is indicated, office visit and estimated conception dates are entered at 394. If an accident is indicated, the operator enters the office visit and accident dates and type of accident at 396.

At 400 the operator initiates a cycle to enter each type of medical service(s) performed, e.g. consultation, disability, follow-up to prior illness, hospitalization, job related, return to work examination, emergency services, laboratory work, or professional courtesy. If a medical consultation is indicated, the consulting physician's identification number is indicated at 402. If the medical diagnosis is a disability and claims for disability insurance are entered at 404, the operator further indicates at 406 enters whether the disability is total or partial and at 408 enters the beginning and ending dates of the disability.

An indication that the office visit was a follow-up to a prior illness may be entered at 410. If the patient is hospitalized, a hospitalization stay is indicated at 412 and the dates of the stay are entered at 414. If the office visit is indicated 416 as being job related, the nature of the job related examination is entered such as a routine examination for potential injury to due toxic substances in the work place, for continued ability to perform high stress or mentally exacting job functions or the like.

If the office visit results in an indication that the patient can return to work, the indication is entered at 420 and the date of return at 422. At 424, the operator indicates whether an disability was involved. If there was a disability involved, the operator enters at 426 whether the disability was job related, i.e. whether workman's compensation may be involved. At 428 the operator enters whether the disability was total or partial and at 430 the beginning and ending date of the disability.

At 440 the operator indicates whether an emergency procedure was performed. If the bill is for laboratory work, an indication of the laboratory work performed is entered at 442. If the medical services were performed as a professional courtesy, i.e. no charge, that is indicated at 444.

After the operator has entered the description of the type of medical services provided, the operator indicates at 450 whether additional services were provided as a part of the office visit. If additional services were provided, the program cycles one or more times through the type of visit routines until all performed services are described. After all types of services have been indicated, then at 452 the routine cycles through a diagnosis entry procedure until each diagnosis is entered. If a consultation only is made, that is indicated at 454. If diagnoses were made by the physician, the diagnoses are entered at 456. For each diagnoses, the treatment procedures utilized are indicated in a treatment procedure routine starting at 458. More particularly to the preferred embodiment, the medical service dates are indicated at 460, the location at which the services were performed at 462, any non-office services at 464, the type of service at 466, the fees at 468, and the number of occurences at 470. At 472, the operator indicates whether any additional procedures were performed for a given diagnosis. At 474, the routine determines whether any additional diagnoses are to be entered.

At 480 the amount paid directly by the patient is entered. At 482 the operator may elect whether to file the claim or review the entered claim data. If the claim data is to be reviewed and the program returns to step 370. If the claim is to be filed, an automatic dial routine is retrieved from memory and the central processing system is dialed at 484. At 486, the physician's identification code is read either from memory in the terminal or by moving the physician identification card past the card reader 12. The entered data is compiled at 488 and transmitted at 490 on the telephone or other interconnecting communication lines. The terminal holds the communication lines until an acknowledgement, error signal, or other response is received at 492 from the central processing system. After the response from the central processing system is displayed at 494, the terminal returns to the ready state 40.

Figure 10:
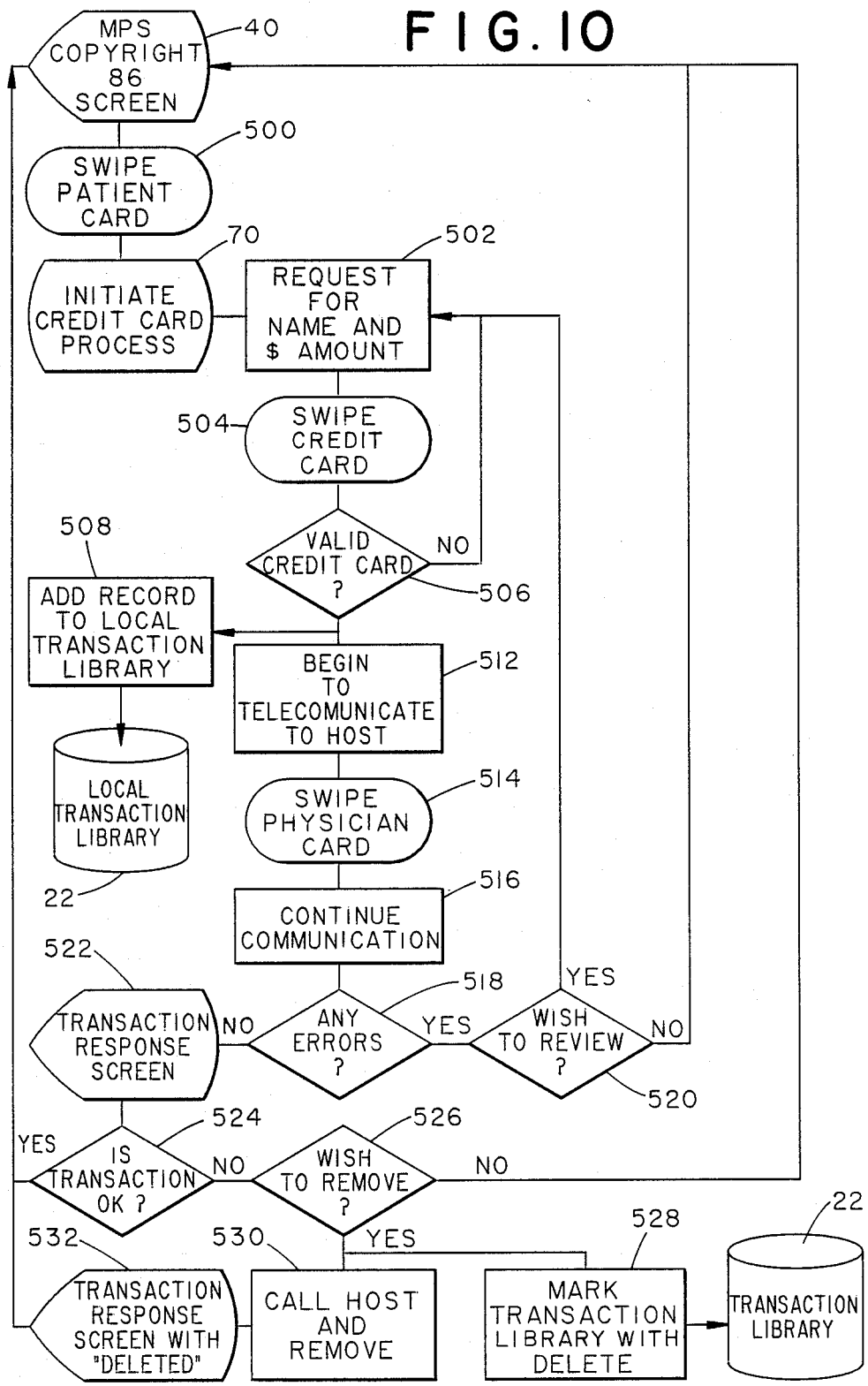
FIG. 10 is a detailed illustration of the data processing at the physician's terminal during a credit card transaction.

With reference to FIG. 10, the operator at 500 swipes the patient card past the swipe reader 12. The operator depresses the credit card key 70 to initiate a credit card transaction. At 502, the operator enters the name and dollar amount and at 504 moves the credit card past the swipe reader. A credit card validity check 506 makes an initial determination of whether the credit card is valid. The validity check may compare redundant information from the card, compare the name read at 500 or the name entered at 502 with the name on the card, or the like. If the card is invalid, it returns to step 502. If the card passes the validity test, the record of the patient identification, credit card transaction, amount, medical service and the like are entered at 508 on the local transaction library file 22 to store a record of the transaction.

A program 512 effects an automatic dial up or otherwise initiates a telecommunication process with the central computer system. The physician identification is supplied at step 514, preferably by running the physician's identification past the swipe reader 12. At 516, the entered credit card information is communicated to the central computer system and the telecommunication line is held open awaiting an acknowledgement or error message. When the acknowledgement or error message is received, a means 518 determines whether or not any transaction errors were noted by the central processor. If errors were noted, a means 520 gives the operator the opportunity to review the communicated information and make any appropriate changes by returning the program to step 502. If the operator does not wish to review the transaction, the program returns to the ready state to await the next transaction. If there are no errors reported, a transaction response screen 522 displays the acknowledgement and an indication of the transaction which has been completed. The operator is given the opportunity at 524 to approve the transaction or cancel it. If the transaction is approved, the program returns to the ready state. If the transaction is not approved, the operator is given the opportunity at 526 to delete the transaction. If the transaction is to be deleted, a means 528 causes the transaction recorded in the local transaction library file 22 to be marked as deleted, although a record of the deleted transaction is retained. A telecommunications step or means 530 causes the central or host computer to delete the transaction. Upon completion of the deletion process, the central computer system provides an acknowledgement which is displayed at 532 indicating that the transaction has been deleted.

With reference to FIG. 11, the operator may elect to review transactions stored in the transaction memory or library file 22 by depressing the transaction review key 74. Depressing the transaction review key causes a library menu to be displayed at 540 from which the operator may select to review all transactions, a specific reference number transaction, a transaction summary report, or to erase a library transaction.

If the operator elects at 542 to review all transactions, a subroutine 544 commences retrieving each transaction with the most recent transaction first and displaying the transactions serially on the display means 14. As each transaction is displayed, the operator indicates at 546 whether or not the transaction is approved. If approved, the next transaction is retrieved at 548 and the process is repeated until a last transaction detecting means 550 determines that the last transaction stored in the transaction library file 22 has been retrieved. If a transaction is not approved, the operator indicates at 552 whether the disapproved transaction should be deleted. If the transaction is to be deleted, a routine 554 requires that the physician's card be read and then proceeds to call the central processor to delete the transaction. A subroutine 356 marks the deleted transaction in the transaction library file 22 as having been deleted.

If the operator wants to delete or review a specific transaction, a transaction sort means 560 receives an indication of the transaction to be reviewed and compares each stored transaction with the indicated transaction. Upon locating and displaying the selected transaction, a means 562 provides the operator with the opportunity to determine whether to remove the transaction. If the transaction is not to be removed, the program returns to the ready state. If the transaction is to be deleted, a means 564 requires the physician's card to be read, accesses the central computer, and causes the transaction to be deleted therefrom. A means 566 marks the transaction as deleted in the transaction library file 22.

If the operator requests a report at 570, the operator is given the opportunity at 572 to decide whether the report should be printed or displayed on the display 14. If the display is to be printed, a report generating means 574 retrieves the appropriate information from the transaction file, sorts the information, calculates totals and subtotals, and otherwise compiles the retrieved information into a preselected report format. The compiled data is conveyed to the printer and printed at 576. If the data is to be displayed on the display, a report generator 578 causes the appropriate transaction information to be retrieved and formated into a preselected report format. A display means control 580 causes the report to be displayed on the display means 14. After the report has been produced, the operator indicates at 582 whether the data stored in the transaction library memory 22 is to be erased. If the data is to be erased, a transaction file erasing means 584 erases the data from the transaction library file 22 of the terminal. The corresponding records at the central processing system are not erased.

If the operator wants to erase the transaction library file 22, an erase program 590 is entered. A double check means 592 requires the operator to confirm that the entire transaction library memory is to be erased. If the operator confirms that the transaction library file 22 is to be erased, a transaction library erasing routine 594 deletes the data from the transaction library memory 22.

Figure 12:
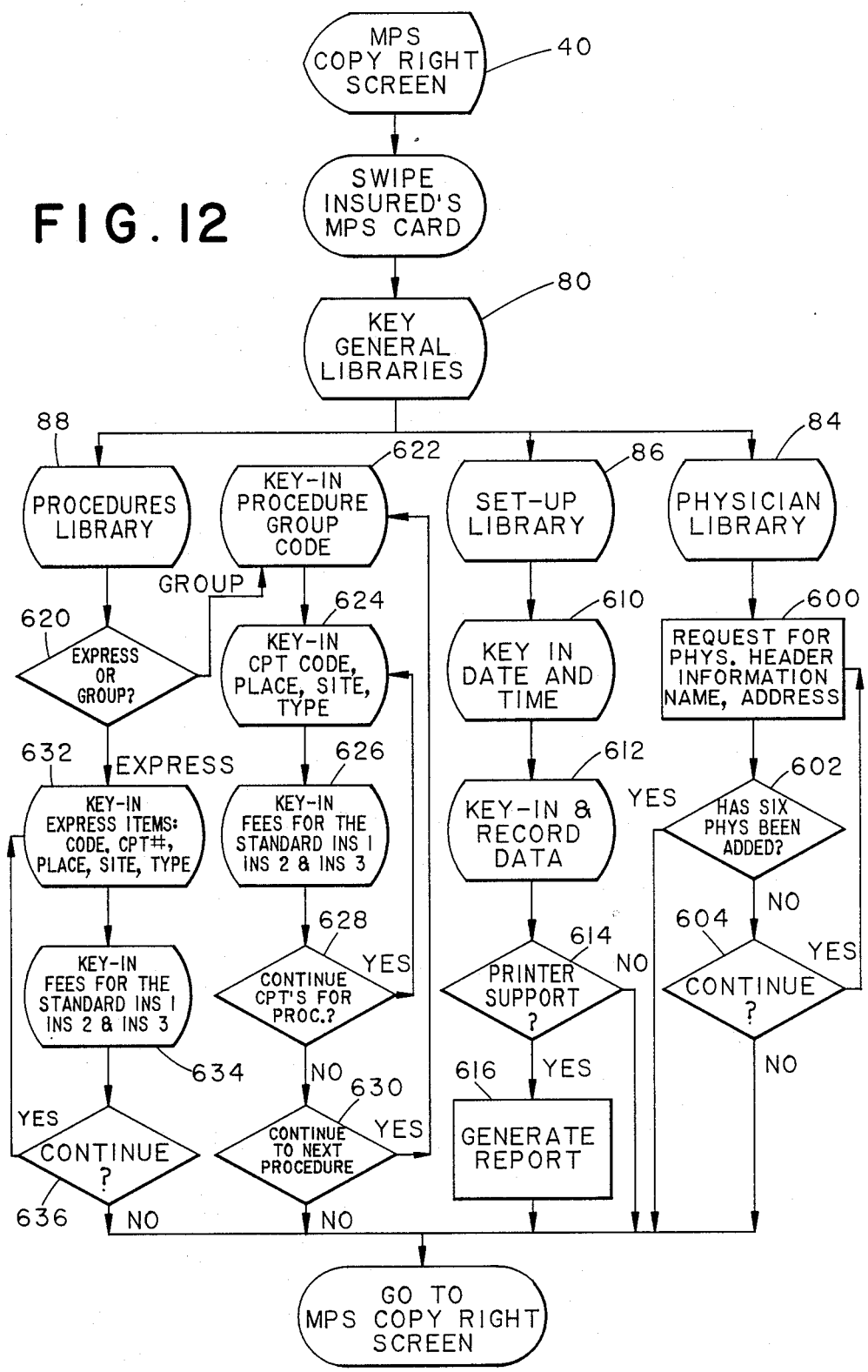
FIG. 12 is a detailed illustration of the library access data processing procedure at the physician's terminal.

With reference to FIG. 12, if the operator selects the general libraries key 80, the operator again may select the physician library 84, the set-up library 86, or the procedures library 88. If the physician library 84 is selected, the operator at 600 may provide a request for previously stored physician information, i.e. name, address, and other appropriate information. A physician information request limiting means 602 determines whether information on more than a preselected number of physicians has been supplied. If not, a means 604 gives a physician the opportunity to terminate the physician information retrieval process or request additional physician information.

If the physician wants to set-up a new library, i.e. the set-up library procedure 86, the operator first keys in the date and time at 610. At 612, data entered in the library might store phone numbers, touch tone automatic dial procedures, serial numbers, service sites, physician numbers, patient numbers, and the like. Once the library is set-up and data is entered or modified, the operator indicates at 614 whether or not a printed record of the stored data is to be provided. If a printed record is to be provided, a report generator 616 generates an appropriate paper report.

If the procedures library 88 is selected, the operator may enter supporting information for the most commonly performed treatments in the physician's practice. At 620, the physician selects whether the speed claim transaction information is to be entered for a group of medical procedures or for express items. If the procedure group is selected, the operator keys in the procedure group code at 622 to designate the group of procedures. At 624, the operator keys in the specific treatment code, the site on the patient's body where the treatment is performed, a type of treatment, a physician's treatment code, and other information which is required by the insurance companies but is standard each time the treatment is performed. At 626, the operator keys in the fees for performing the treatment. More specifically, the operator keys in the physician's standard fee as well as the fees which are to be charged to patients insured by each of a plurality of insurance companies. In this manner, the physician may choose to charge some patients less than the standard fee so that the procedure will be fully covered by insurance. At 628, the operator elects whether to enter additional treatments within the procedure group. At 630, the operator elects whether to enter the standardized claim data for another group of procedures.

If the operator elected the express procedure at 620, then the procedure group step is eliminated. At 632, the operator enters the treatment and the standard information concerning the treatment, such as the type of treatment, the site on the patient's body that is treated, the place where the treatment takes place, and the like. At 634, the operator keys in the physician's standard fee and the fees for each of a plurality of insurance companies. At 636, the operator elects whether to enter information for additional treatments.

Figure 13:
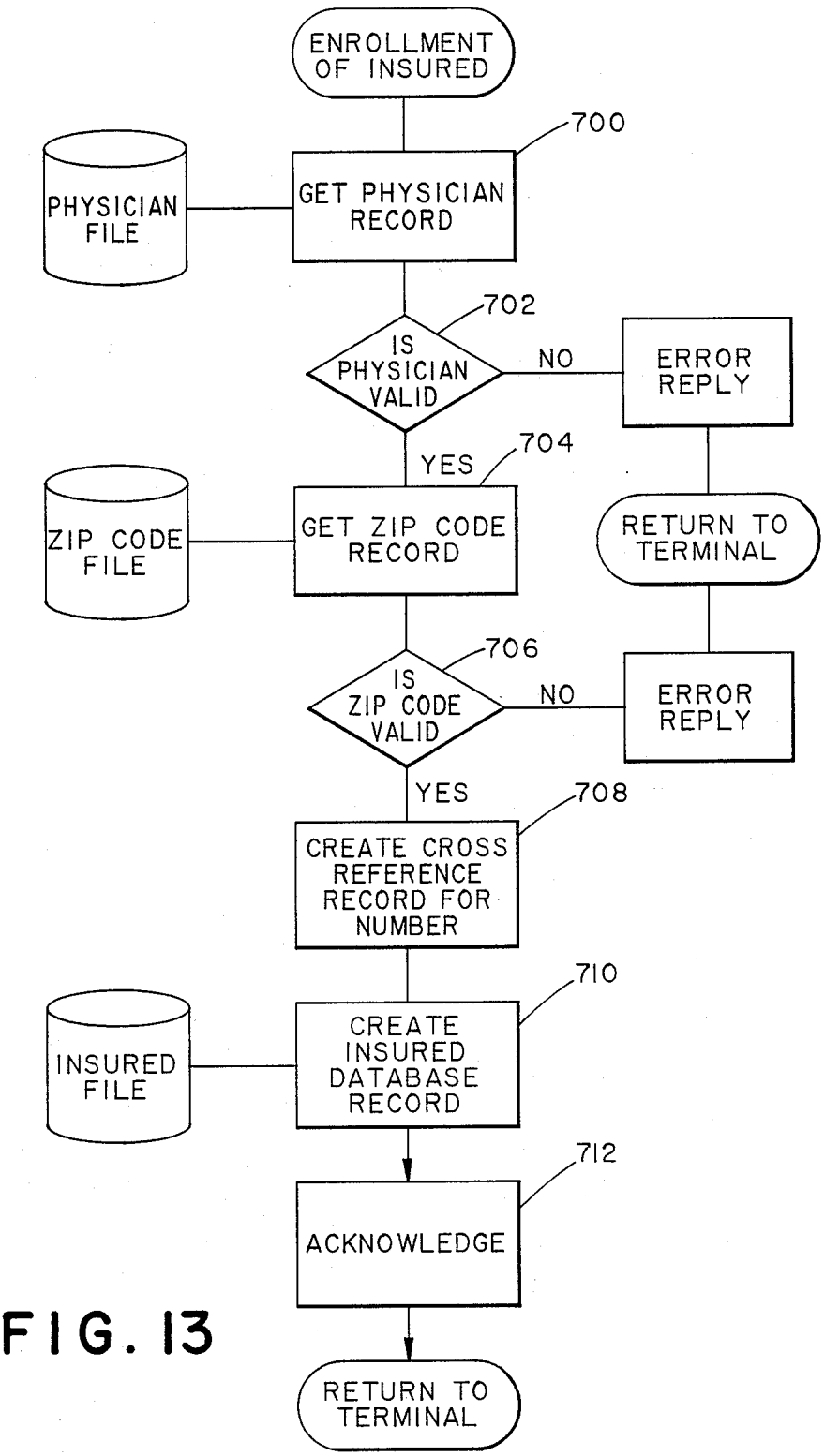
FIG. 13 is a detailed illustration of the sign-up transaction process in the central processing system.

With reference again to FIGS. 1 and 5 and particular reference to FIG. 13, a patient is signed at the remote terminal during the sign-up process 56 illustrated in greater detail in FIG. 7. Upon receiving the sign-up information at the central processing system, a means 700 retrieves the corresponding physician record. A physician validating means 702 determines whether the sign up is being made by a valid participating physician. If not, an error signal is generated and sent to the remote terminal. A zip code record is retrieved from the zip code file at 704 and used to validate an incoming record at 706. A cross reference entry is created at 708 to cross reference the physician record with a patient identification. The appropriate record is created at 710 in the insured data base or file to store the received sign-up data therein. An acknowledgement is generated at 712 and the machine returns to ready for the next operation.

Figure 14:
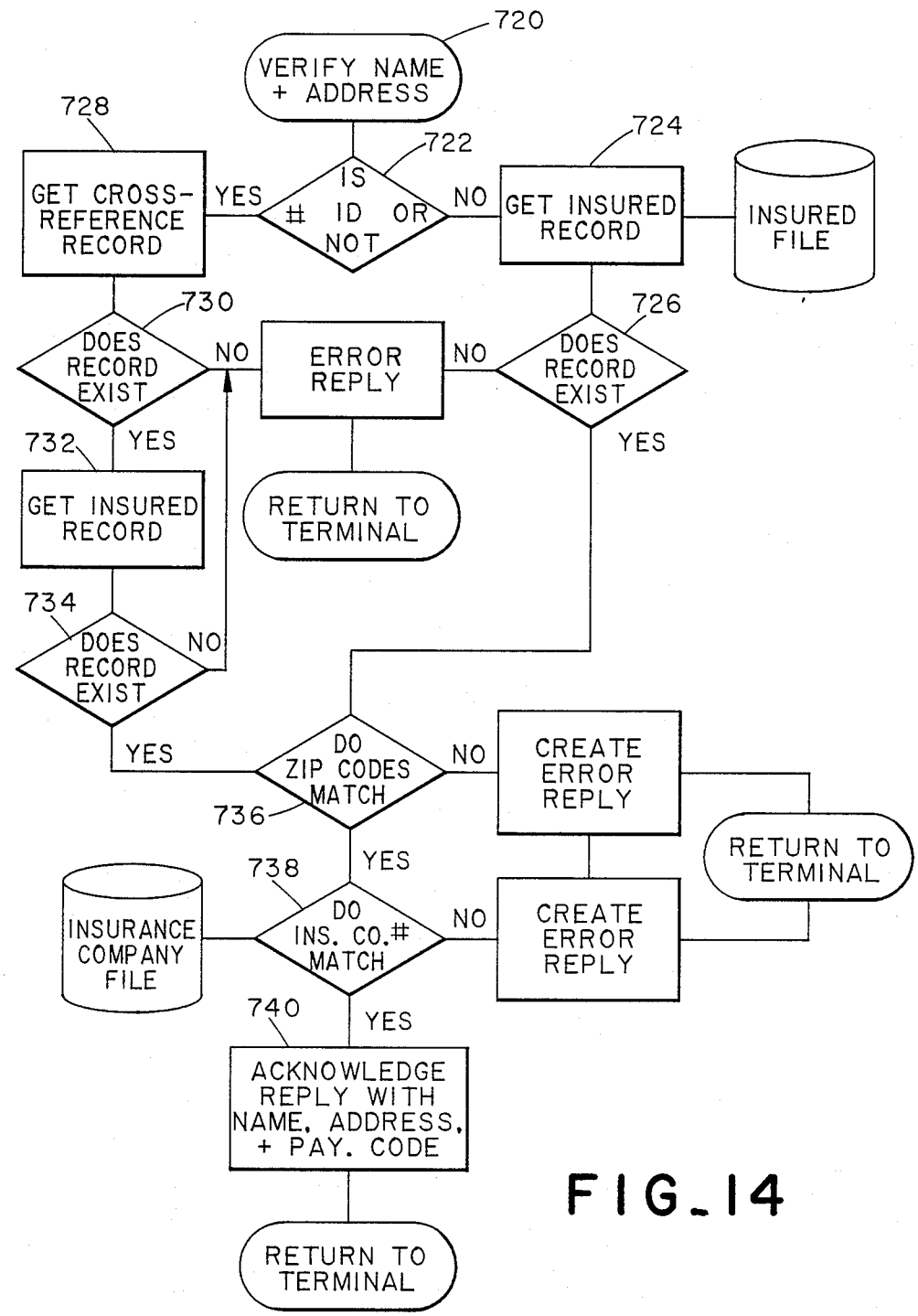
FIG. 14 is a detailed illustration of the enrollment verification process at the central processing system.

If enrollment is to be verified, the remote terminal procedure was as set forth above in conjunction with FIG. 8. With reference to FIG. 14, the central processing system receives the enrollment information at 720 for verification. A patient identification number validating means 722 determines whether or not the patient identification number to be verified is, in fact, of the appropriate form and format to be a patient identification number. If the patient identification number is valid, a record retrieval means 724 uses the patient identification number to retrieve the corresponding patient record and a comparing means 726 determines whether or not a corresponding patient record exists. If the patient identification number is not proper, other portions of the patient identification are utilized to access a cross reference file 728. From the cross reference, the appropriate patient record is identical. A comparing means 730 determines whether the cross reference file, in fact, has a cross reference for the enrollment data to be verified. If a cross reference does exist, the cross reference information is utilized at 732 to retrieve the appropriate insured's record. A record comparing means 734 verifies that a corresponding patient record does, in fact, exist and has been retrieved.

Having retrieved a patient record, a series of verifications are made to assure that the correct record has been retrieved and that the retrieval is authorized. First, a zip code verifying means 736 compares zip codes from the retrieved record and the enrollment information to be verified. If the zip codes match, then insurance company identifications from the two records are compared by an insurance company comparing means 738. If either the zip code or the insurance companies fail to match, appropriate error signals are created and returned to the physician's office terminal. If the series of verifications show that the enrollment to be verified is, in fact, correct, an acknowledgement means 740 acknowledges verification and returns recorded information concerning the patient for whom verification was requested, such as name, address, treatment history, and the like.

Figure 15:
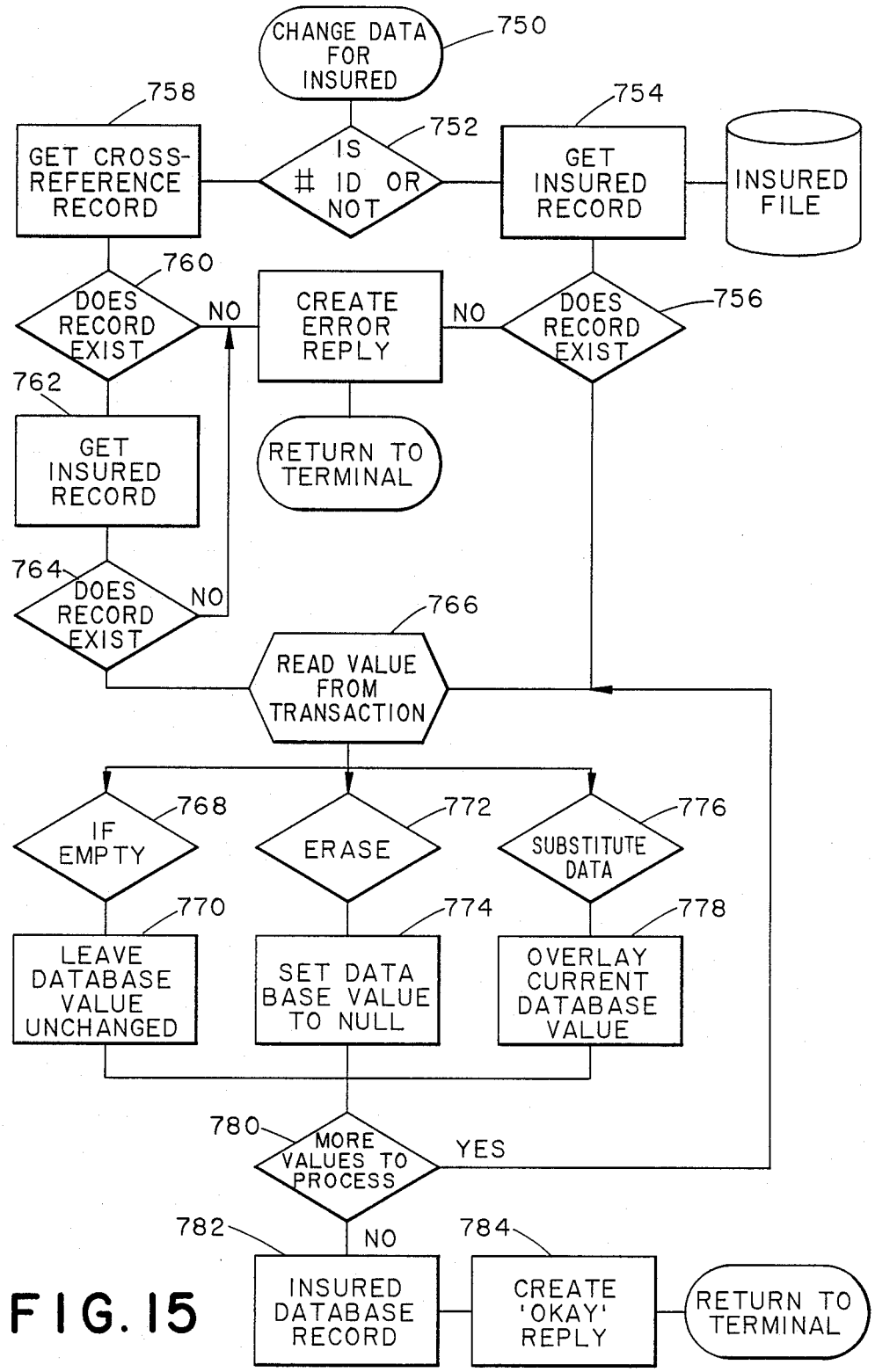
FIG. 15 is a detailed illustration of the transaction change process at the central processing system.

With reference to FIG. 15, when the change of enrollment data procedure 54 is invoked, the central processor receives the change data at 750. A patient identification number comparing means 752 reviews the incoming change data to determine whether or not the patient identification number is present. If an identification number is present, the ID number is used by a record retrieving means 754 for retrieving the patient record. A record existence verification means 756 verifies that a record is, in fact, available and retrieved. If no valid identification is present, a cross reference means 758 utilizes other patient identification information to access a cross reference table to determine the patient number. A record existence determining means 760 determines whether or not there is a cross referenced patient identification number in the cross reference file. If an identification number is retrieved, a record retrieval means 762 retrieves the corresponding record whose existence is verified by a record verification means 764. If any of the patient numbers or records are missing, an error signal is returned to the remote terminal. If the patient's record is verified, a read means 766 reads change orders received from the remote terminal. If a change field of the change order is empty, the corresponding field in the patient data base or file remains unchanged. If a delete command is read by a comparing means 772, the corresponding stored data base field is emptied or nulled by a write means 774. If the field has information of a recordable nature, as determined at 776, a write means 778 overlays or replaces the data in the patient file with the corresponding received substitute data. After each change is entered, an end of change determining means 780 determines if additional changes are to be made to the retrieved patient record. If no additional changes are to be made, the revised patient record is returned to the patient file or data base at 782. At 784, an acknowledgement is returned to the remote terminal for display to the operator.

Figure 16A:
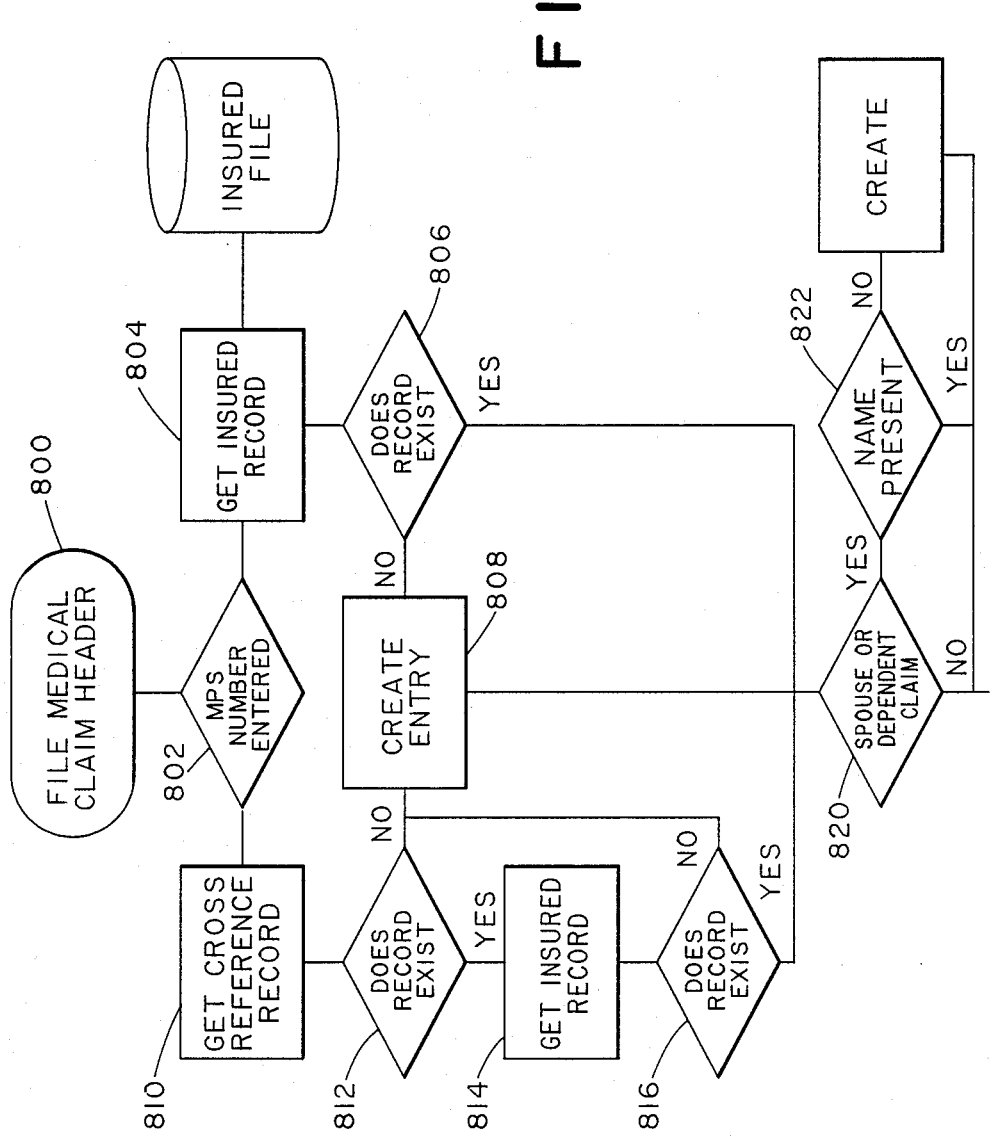
FIG. 16 is a detailed illustration of the claim entry data processing at the central processing system.
Figure 16B:
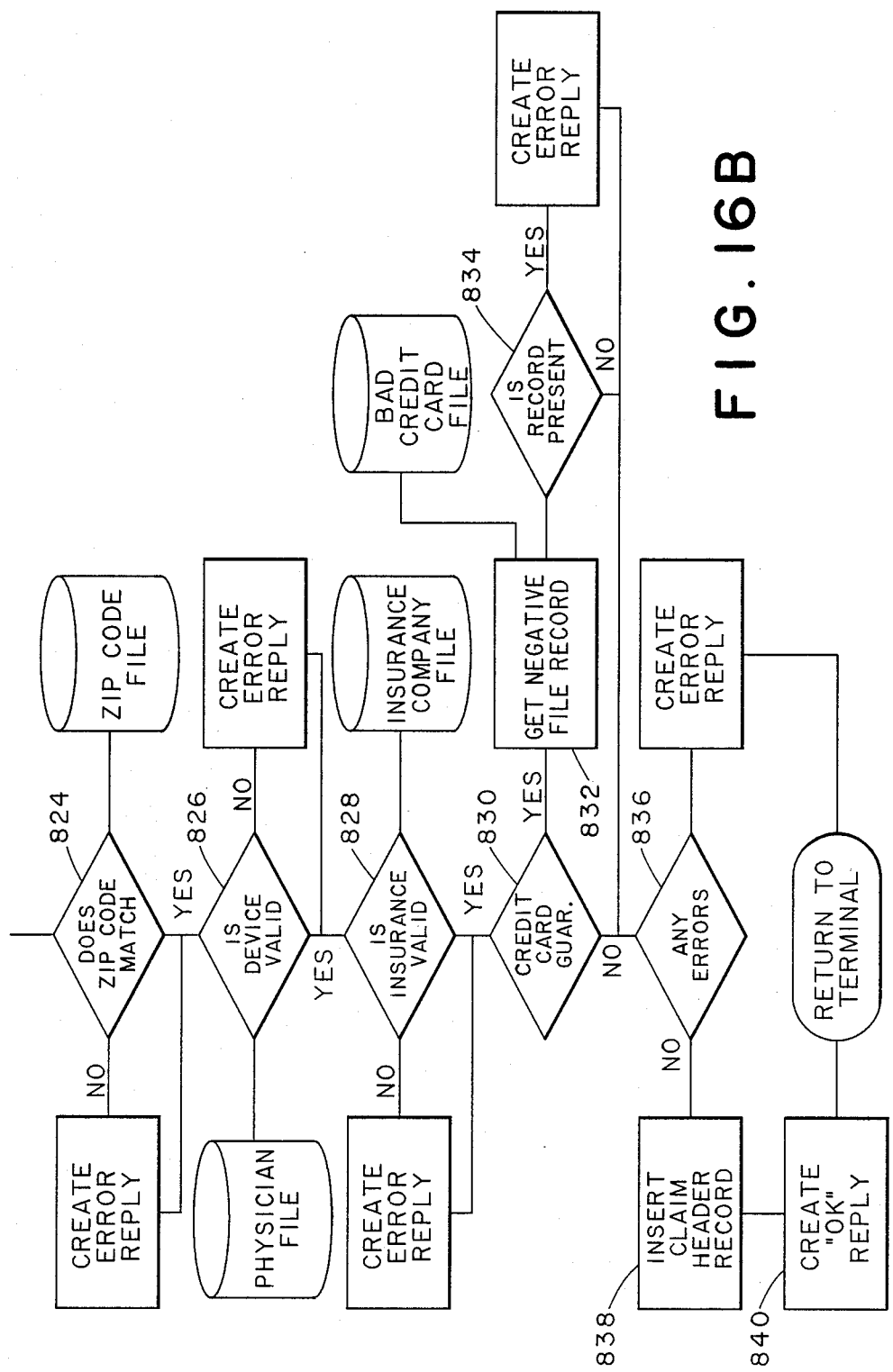

With reference to FIG. 16, upon receipt of a medical claim at the central processing system B, the medical claim is held at 800. A comparing means 802 compares information in the claim to determine whether an appropriate patient identification is provided. If the patient identification is present, the patient number is used to address the patient files at 804. A verification means 806 determines whether or not the patient number does, in fact, exist and whether a corresponding patient record is successfully retrieved. If no patient record is retrieved, an error signal is returned to the terminal at 808.

If there is no patient identification number in the claim, then other patient information is used to address a cross reference table 810. A comparing means 812 determines whether a cross reference to a patient record exists. If there is a cross reference, the crossed referenced record is retrieved at 814. Another comparing means 816 verifies that the cross referenced record exists and has been satisfactorily retrieved.

At 820, the system checks whether the medical service payment claim is for a spouse or dependent of an insured. A comparing means 822 compares the spouse or dependant information, with information stored in the insured file, to verify that the spouse or dependent is insured. A zip code verification means 824 compares an entered zip code that is a part of the claim header, with zip code information for the patient stored in the central processing system zip code file as a check on the validity of the entered data. A portion of the claim header which identifies the terminal is compared at 826 with a terminal list to validate whether the claim arose on a valid remote terminal. An insurance comparing means 828 compares the insurance information from the header with the information from the insured and insurance companies files to validate that the patient still has the asserted insuranced coverage. A credit card guarantee means 830 determines whether or not payment is being guaranteed by a credit card. If so, a current bad credit card file 832 is accessed and the credit card number comparing means 634 compares the credit card number with the bad credit numbers to be sure that a genunine and valid credit card is guaranteeing the payment. An error comparing means 836 determines whether there are any errors in the claim. If not, the claim information is filed in the appropriate insurance company, physician, and insured files at 838. An acknowledgement of the completed transaction is generated at 840 and returned to the terminal so that the next claim or procedure may be commenced.

Figure 17:
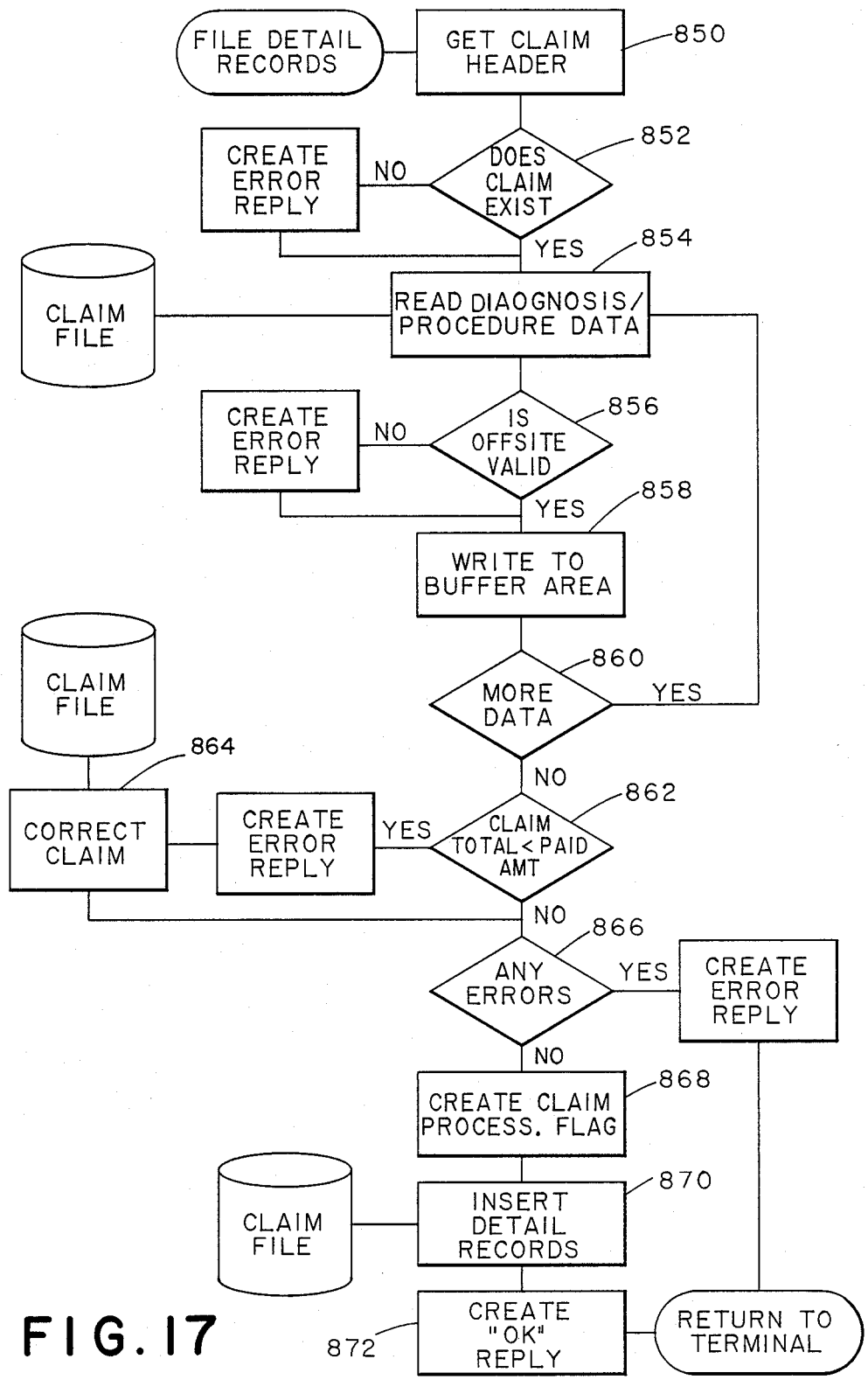
FIG. 17 is a detailed illustration of the line item entry process at the central processing system; and, FIG. 18 is a detailed illustration of the credit card charge process at the central processing system.

With reference to FIG. 17, an individual line item change to a claim can be made. The claim header for the claim which is to be changed is received at 850 and utilized to address the claim file to determine that the claim to be changed, in fact, exists. A claim verification means 852 provides an error signal to the remote terminal if the claim does not exist. The diagnosis and procedure data including the site at which the services were rendered is read from the claim file at 854. The claim change origin site is compared with the retrieved site information at 856 to verify that the change is authorized. The claim data is written into a buffer storage area at 858. A comparing means 860 determines whether additional changes are to be entered. The revised claim payment amount is compared at 862 with the amount of the original claim. If the new total is less than the paid amount, the original claim header is deleted from the claim file at 864 and replaced with the revised claim. An error detecting means 866 determines whether there are any errors in the revised claim and, if so, produces an appropriate display to the remote terminal operator. At 868, a supplemental claim is created. The supplemental or revised claim may be for the additional fees by which the amended procedure has increased the claim or a complete new claim. The revised claim is inserted into the claim file at 870 and acknowledgement is sent to the remote terminal at 872.

Figure 18:
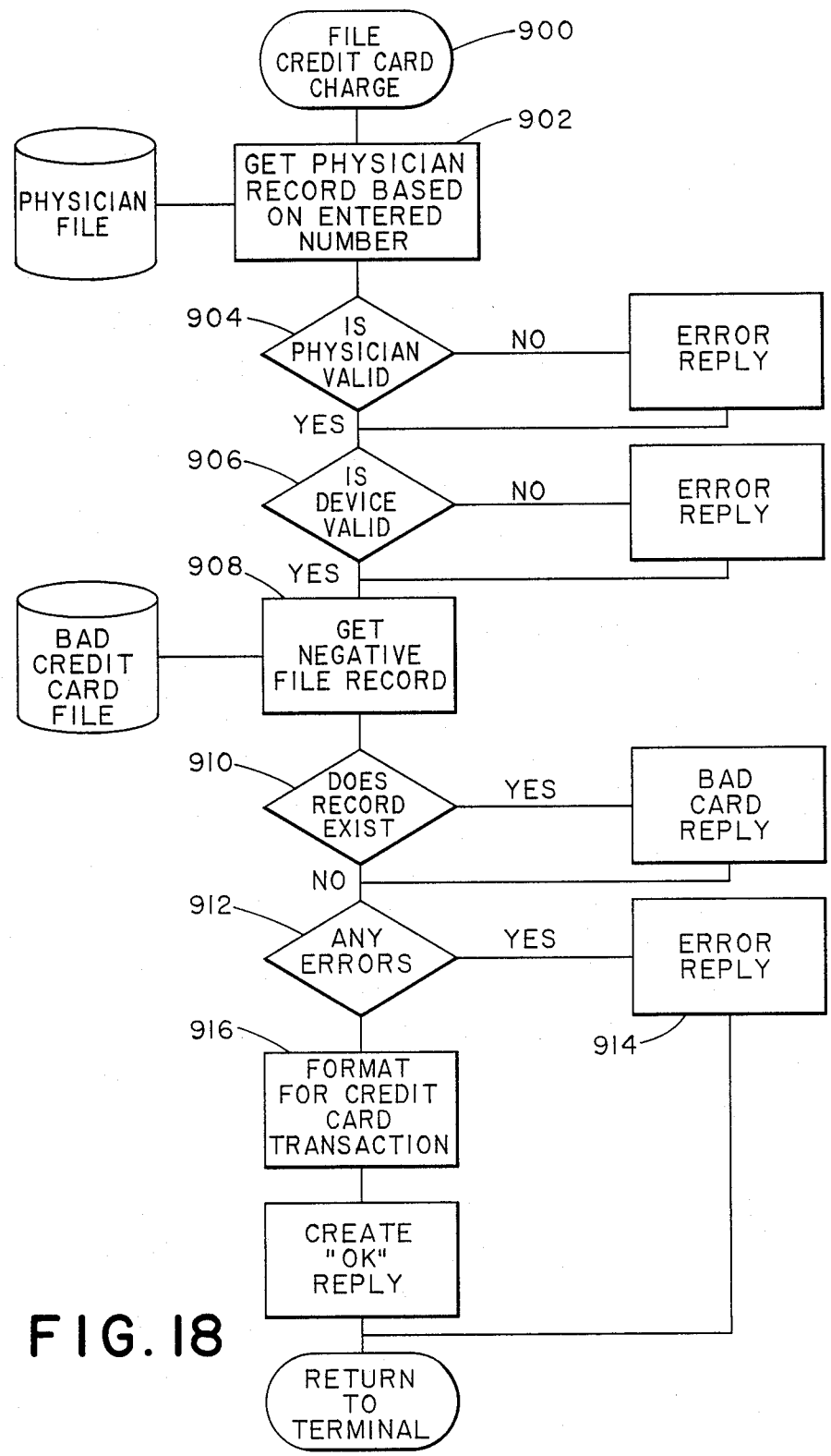

With reference to FIG. 18, if a credit card transaction is processed by the remote terminal as illustrated in FIG. 11, the credit card information is received by the central processing unit at 900. A physician identification from the entered credit card transaction is retrieved at 902 and compared with previously stored valid physician identifications at 904. A terminal identification is compared with valid terminal identifications at 906 to assure that the transaction is originating at an authorized terminal. If either the physician or the terminal is unauthorized, an appropriate error signal is returned to the remote terminal and the transaction terminated.

If the physician and terminal are authentic, then a negative credit card number record or file indicative of bad credit numbers is accessed at 908. A credit card validation means 910 determines whether the presently addressed credit card number is in the bad credit card file. If the card is bad, a bad card reply is sent to the remote terminal and the transaction is terminated. An error determining means 912 determines whether any errors are present in the credit card transaction. If so, the appropriate error reply is returned to the remote terminal at 914. An appropriate claim is formated for credit card payment at 916. The formated credit card information is set up for forwarding to the credit card company either on tape or by printed invoice.

The invention has been described with reference to the preferred embodiment. Obviously, modifications and alterations will occur to others upon reading and understanding the preceding detailed description of the preferred embodiments. It is intended that the invention be construed as including all such alterations and modifications insofar as they come within the scope of the appended claims or the equivalents thereof.

Having thus described a preferred embodiment, the invention is now claimed to be:

1. A financial transaction system for physician's offices, the system comprising:
 a plurality of physician office terminals for location in physicians' offices, each terminal including a data entry means for entering medical insurance claim electronic data including at least patient identification data, medical service identification data, abbreviated routine medical service codes indicative of regularly performed medical procedures, physician identification data, and insurance carrier identification data, a modem means for transmitting the entered electronic data on a communications medium, and a terminal data processing means for processing the electronic data entered on the data entry means and providing the processed data to the modem means for transmission, the terminal data processing means including:
 a transaction library means for storing a record of entered medical claim data;
 a routine medical procedure library means for storing medical procedure details for services which are regularly performed in a medical procedure memory means, the medical procedure memory means being accessed by the abbreviated routine service codes to retrieve a more complete medical service description electronic data for transmission by the modem means, whereby only the abbreviated routine code is entered to cause a complete service description to be transmitted;
 a physician library means for storing physician identification details which are retrieved for transmission by the modem means, whereby physician identification details need not be entered for each entered medical claim; and,
 a central processing means for receiving data transmitted by the terminal modem means and processing the data to generate medical insurance claims.

2. The system as set forth in claim 1 wherein at least some of the physicians' office terminals further include:
 a transaction report generating means for reading stored claim data from the transaction library memory means and generating an appropriate report of processed claims; and, a printer operatively connected with the transaction report generating means for printing the generated reports.

3. The system as set forth in claim 1 wherein the data entry means includes:
- a keyboard for key entering data; and,
- a swipe reader for reading prerecorded magnetic tape on identification cards.

4. The system as set forth in claim 1 wherein the central processing means includes:
- a patient comparing means for comparing received patient identification data with prerecorded patient identification data in a central patient memory means for validating the authenticity of received patient identification data;
- a physician comparing means for comparing received physician identification data with prerecorded physician identification data in a physician memory means to verify the authenticity of received physician identification data; and,
- a medical claim format means for processing received patient identification data, medical service identification data, physician identification data, and insurance carrier identification data into one of a plurality of preselected insurance claim formats.

5. The system as set forth in claim 1 wherein the physician's office terminal data processing means also includes a credit card means for processing entered credit card data and wherein the central processing means includes a credit card information processing means for processing credit card data received from physicians' office terminals to bill a credit card company for received medical services.

6. The system as set forth in claim 5 wherein the central processing means further includes a funds transfer means for causing a financial institution to transfer monies into physicians' accounts.

7. The financial transaction system as set forth in claim 1 wherein each physician's office terminal further includes:
- in the terminal data entry means, means for entering data concerning patient information, changes for patient information, and changes in medical insurance;
- a terminal electronic memory means for storing data;
- wherein the terminal data processes means processing stored data from the terminal electronic memory means;

and wherein the central processing means further includes:
- a central modem means operatively connected with the electronic data communications medium for receiving electronic data transmitted from the physician's office terminals;
- a central electronic memory means for storing previously entered data concerning at least physicians, patient identifications, patient information, and medical insurance, the central electronic memory means being addressed from the central modem means to store additional patient identification and information and to change previously stored patient information and medical insurance data, whereby patient information in the central processing means is maintained from the remote terminals;
- a central data processing means for processing data received from the central modem and previously stored data from the central electronic memory means to create the medical insurance claims;
- a medical claim communicating means for communicating the processed medical claims to a medical insurance company.

8. The system as set forth in claim 7 wherein each physician's office terminal further includes a display means for displaying instructions to the operator and data from the terminal electronic storage means.

9. The system as set forth in claim 8 wherein each terminal data entry means includes a keyboard for manual entry of data and a magnetic tape reader for reading prerecorded magnetic tape on identification cards.

10. The system as set forth in claim 7 wherein the central processing system means further includes a printer for printing medical insurance claims and other financial records.

11. The system as set forth in claim 7 wherein the medical claim communicating means includes an electronic data transfer means for transferring medical claims in the form of electronic data directly from the central processing system to a computer of a medical insurance company.

12. The system as set forth in claim 7 wherein the central processing system further includes a funds transfer means for conveying instructions to a financial institution to transfer funds into the accounts of each of a plurality of physicians.

13. The system as set forth in claim 7 wherein each physician's office terminal further includes a credit card reading means for reading credit cards and wherein the central processing system includes credit card data processing means for processing credit card data and invoicing credit card companies for medical services charged on a credit card.

14. The system as set forth in claim 1 wherein each physician's office terminal further includes a credit card reading means and wherein the central processing system includes a credit card billing means for billing medical services charged to a credit card to an appropriate credit card company.

15. The financial transaction system as set forth in claim 1 wherein the central processing system further includes:
- a central modem means operatively connected with the electronic data communications medium for receiving the electronic data from the physician's office terminals;
- a patient memory means for storing patient identification data;
- a physician memory means for storing physician identification data;
- an insurance company format memory means for storing claims format information for each of a plurality of insurance companies;
- a patient comparing means for comparing patient identification data received from a terminal with patient identification data retrieved from the patient memory means;
- a physician comparing means for comparing physician identification data received from a terminal with physician identification data retrieved from the physician memory storing means;
- a medical claim formatting means, which is operatively connected with (i) the patient and physician comparing means to be selectively enabled thereby, (ii) the central modem means to receive patient, physician, and medical service identification data therefrom, and (iii) the insurance company format memory means for receiving a corresponding insurance company claims format therefrom, for converting the received patient, physician, and medical service identification data into the retrieved insurance company format; and, a medical insurance claims generating means for generating an insurance claims for transmission to the identified insurance company, the medical insurance claims generating means being operatively connected with the medical claim formatting means.

16. The system as set forth in claim 15 further including a printer operatively connected with the medical insurance claims generating means for printing generated medical claims.

17. The system as set forth in claim 15 further including an electronic data transfer means operatively connected with the medical insurance claims generating means for transferring the generated medical insurance claims directly to an insurance company computer.

* * * * *